United States Patent [19]

Lerner et al.

[11] Patent Number: 5,856,537
[45] Date of Patent: Jan. 5, 1999

[54] INHIBITORS OF OLEAMIDE HYDROLASE

[75] Inventors: Richard A. Lerner, La Jolla; Chi-Huey Wong, Rancho Santa Fe; Dale L. Boger, La Jolla; Steven J. Henriksen, Solana Beach, all of Calif.

[73] Assignee: The Scripps Research Institute, La Jolla, Calif.

[21] Appl. No.: 670,284

[22] Filed: Jun. 26, 1996

[51] Int. Cl.⁶ .................................................. C07C 233/00
[52] U.S. Cl. ........................ 554/61; 554/67; 514/546; 514/549; 514/552; 514/613; 514/625; 514/627; 514/628; 564/248; 568/382; 568/412; 568/417; 568/418; 568/419
[58] Field of Search ................ 554/61, 67; 514/546, 514/549, 552, 613, 623, 627, 628; 564/248; 568/382, 412, 417, 418, 419

[56] References Cited

PUBLICATIONS

Koutek et al, Journal of Biological Chemistry, vol. 269, No. 37, pp. 22937–22940, 1994.
Chem. abstr. of JP–01086884, 111:193095, 1989.
Cravatt, et al., "Chemical Characterization of a Family of Brain Lipids that Induce Sleep", *Science*, 268: 1506–1509 (1995).
Cravatt, et al., "Structure Determination of an Endogenous Sleep–Inducing . . ." *J. Am. Chem. Soc.*, 118:580–590 (1996).
Koutek, et al., "Inhibitors of Arachidonoyl Ethanolamide Hydrolysis", *J. Biol. Chem.*, 269:22937–22940 (1994).
Lerner, et al., "Cerebrodiene: A Brain Lipid Isolated from Sleep–Deprived Cats", *Proc. Natl. Acad. Sci., USA*, 91:9505–9508 (1994).
Maurelli, et al., "Two Novel Classes of Neuroactive Fatty Acid Amides. . .", *FEBS Lett.*, 377:82–86 (1995).

*Primary Examiner*—Paul J. Killos
*Assistant Examiner*—Deborah D. Carr
*Attorney, Agent, or Firm*—Donald G. Lewis

[57] ABSTRACT

Inhibitors of oleamide hydrolase, responsible for the hydrolysis of an endogenous sleep-inducing lipid (1, cis-9-octadecenamide) were designed and synthesized. The most potent inhibitors possess an electrophilic carbonyl group capable of reversibly forming a (thio) hemiacetal or (thio) hemiketal to mimic the transition state of a serine or cysteine protease catalyzed reaction. In particular, the tight binding α-keto ethyl ester 8 (1.4 nM) and the trifluoromethyl ketone inhibitor 12 (1.2 nM) were found to have exceptional inhibitory activity. In addition to the inhibitory activity, some of the inhibitors displayed agonist activity which resulted in the induction of sleep in laboratory animals.

14 Claims, 14 Drawing Sheets

| # | Inhibitor | $K_{i,app}$ (µM) | | # | Inhibitor | $K_{i,app}$ (µM) |
|---|---|---|---|---|---|---|
| 1 | H₂N-C(O)-R oleamide | $K_m = 5 \pm 2$ µM | | | R = C₁₆H₃₂ (with cis double bond) | |
| Oleic acid | HO-C(O)-R | 6.0 | | 12 | F₃C-C(O)-CH₂-R | 0.0012 ± 0.0004 |
| 2 | HO-NH-C(O)-R | 5 ± 1 | | 13 | F₃C-C(O)-R | 0.002 ± 0.0006 |
| 3 | Cl-CH₂-C(O)-R | 0.7 ± 0.3 | | 14 | F₃C-C(O)-CH₂-R (trans) | 0.009 ± 0.003 |
| 4 | H-C(O)-R | 0.19 ± 0.06 | | 15 | F₃C-C(O)-CH₂-R (saturated) | 0.023 ± 0.007 |
| 5 | H-C(O)-R | 0.04 ± 0.01 | | 16 | MeO-CH(OMe)-CH₂-R | > 300 |
| 6 | H₂N-C(O)-C(O)-R | 0.016 ± 0.005 | | 17 | H₂N-C(O)-CH(OH)-R | > 100 |

FIG. 1A

| # | Structure | Value |
|---|---|---|
| 7 | R-C(=O)-CH2-C(=O)-NH2 | 0.017 ± 0.006 |
| 8 | R-C(=O)-C(=O)-OEt | 0.0014 ± 0.0005 |
| 9 | R-C(=O)-CH2-C(=O)-OEt | 0.009 ± 0.003 |
| 10 | R (saturated)-C(=O)-CH2-C(=O)-OEt | 0.012 ± 0.003 |
| 11 | CH3(CH2)14-C(=O)-C(=O)-O-t-Bu · H2O | 0.150 ± 0.040 |
| 18 | R-CH(OH)-C(=O)-OH | 5 ± 2 |
| 19 | R-CH(Cl)-C(=O)-NH2 | > 100 |
| 20 | R-CH(Cl)-C(=O)-OH | 0.3 ± 0.1 |
| 21 | R-CH2-C(=O)-CH=N2 | 13 ± 4 |
| 22 | R-C(=O)-NH-NH2 | Insoluble |

FIG. 1B

| Agent | 1H or 13C NMR Signal | CDCl3 (δ) | CD3OD (δ) | acetone-d6 (δ) | acetone-d6 + D2O (δ)[a] |
|---|---|---|---|---|---|
| 4 | 1H (α-CH2) | 2.40 | 2.42, 1.56 | 2.41 | no change |
|  | 1H (CHO) | 9.73 | 9.69 (53%), 4.46 (47%) | 9.71 | no change |
|  | 13C (C=O) | 202.8 | 204.7, 99.9 | 202.5 | no change |
| 6 | 1H (α-CH2) | 2.89 | 2.81 (52%), 1.75 (48%) | 2.83 | no change |
|  | 13C (1C=O) | 161.9 | 165.2, 176.2 | 163.4 | no change |
|  | 13C (2C=O) | 198.6 | 200.0, 100.1 | 200.0 | no change |
| 8 | 1H (α-CH2) | 2.81 | 2.81 (25%), 1.78 (75%) | 2.79 | no change |
|  | 13C (1C=O) | 161.3 | 162.5, 172.4 | 162.1 | no change |
|  | 13C (2C=O) | 194.8 | 195.8, 100.0 | 195.1 | no change |
| 12 | 1H (α-CH2) | 2.68 | – (0%), 1.65 (100%) | 2.87 (91%), 1.75 (9%) | 2.82 (9%), 1.60 (91%) |
|  | 13C (C=O) | 191.6 | 97.3 | 192.3, 94.2 | 93.8 |
|  | 13C (CF3) | 115.6 | 125.2 | 116.5, 125.2 | 125.0 |

[a] 7% D2O in acetone-d6.

FIG. 2

$$Rate = \frac{[H^+]^3 \nu_{H_3E} + [H^+]^2 K_1 \nu_{H_2E} + [H^+] K_1 K_2 \nu_{HE} + K_1 K_2 K_3 \nu_E}{[H^+]^3 + [H^+]^2 K_1 + [H^+] K_1 K_2 + K_1 K_2 K_3}$$

$$H_3E \underset{}{\overset{K_1}{\rightleftharpoons}} H_2E + H \underset{}{\overset{K_2}{\rightleftharpoons}} HE + 2H \underset{}{\overset{K_3}{\rightleftharpoons}} E + 3H$$

FIG. 12

INHIBITORS OF OLEAMIDE HYDROLASE

SPECIFICATION

1. Field of the Invention

The invention relates to inhibitors of oleamide hydrolase and to agonists with respect to oleamide induced sleep. More particularly, the invention relates to transition-state-mimetics and mechanism-based oleamide derivatives which display inhibitory activity with respect to oleamide hydrolase and/or agonist activity with respect to oleamide induced sleep.

2. Background of the Invention

Oleamide (1, cis-9-octadecenamide) is a naturally occurring brain constituent that has been shown to accumulate and disappear under conditions of sleep deprivation and sleep recovery, respectively (Cravat et al., *Science* 1995, 268, 1506–1509; Lerner et al., *Proc. Natl. Acad. Sci. U.S.A* 1994, 91, 9505–9508; Cravatt et al., *J. Am. Chem. Soc.* 1996, 118, 580–590). In a structurally specific manner, 1 has been shown to induce physiological sleep in animals at nanomolar quantities when injected intravascularly (Cravat et al., *Science* 1995, 268, 1506–1509). Hydrolysis of 1 by an enzyme (oleamide hydrolase) present in the cell membrane rapidly degrades oleamide to oleic acid (cis-9-octadecenoic acid). In an effort to isolate a regulatory agent responsible for controlling endogenous concentrations of 1, an integral membrane protein, oleamide hydrolase, was found to catalyze the hydrolytic degradation of oleamide to give oleic acid (cis-9-octadecenoic acid) and ammonia (FIG. 3), neither of which demonstrate somnolescent activity (Cravat et al., *Science* 1995, 268, 1506–1509).

It has been found that oleamide hydrolase can be inhibited by phenylmethylsulfonyl fluoride, 4,4'-dithiodipyridine disulfide (a potent disulfide forming reagent), and $HgCl_2$ ($IC_{50}$= 700 nM, $K_{i,\ app}$=37 nM), but not by 1 mM EDTA. This suggests that a thiol is intimately involved in the catalytic process and that the enzyme may be a cysteine amidase or possibly a serine amidase with an active site cysteine residue.

A variety of tight binding or irreversible inhibitors of serine and cysteine proteases have been described. These include irreversible inhibitors such as halomethyl ketones (Kettner et al., *Biochemistry* 1978, 17, 4778–4784; Kettner et al., *Thromb. Res.* 1979, 14, 969–973; C. Giordano, et al., *Eur. J. Med. Chem.* 1992, 27, 865–873; Rauber et al., *Biochem. J.* 1986, 239, 633–640; Angliker et al., *Biochem. J.* 1987, 241, 871–875), Michael acceptors (Hanzlik et al., *J. Med. Chem.* 1984, 27, 711–712), epoxides (C. Parkes, et al., *Biochem. J.* 1985, 230, 509–516), O-acyl hydroxylamines (Brömme et al., *Biochem. J.* 1989, 263, 861–866) and diazomethylketones (Green et al., *J. Biol. Chem.* 1981, 256, 1923–1928) as well as reversible transition state mimetic inhibitors such as ketones (Mehdi, S. *Bioorg. Chem.* 1993, 21, 249–259), aldehydes (Westerik et al., *J. Biol. Chem.* 1972, 247, 8195–8197), cyclopropenones (Ando et al., *J. Am. Chem. Soc.* 1993, 115, 1174–1175) and electron-deficient carbonyl compounds such as trifluoromethyl ketones (Wolfenden et al., *Annu. Rev. Biophys. Bioeng.* 1976, 5, 271; Gelb et al., *Biochemistry* 1985, 24, 1813–1817; Imperiali et al., *Biochemistry* 1986, 25, 3760–376; Koutek et al., *J. Biol. Chem.* 1994, 269, 22937–22940), α-keto acid derivatives (Li, Z. et al., *J. Med. Chem.* 1993, 36, 3472–3480; Harbeson et al., *J. Med. Chem.* 1994, 37, 2918–2929; Peet et al., *J. Med. Chem.* 1990, 33, 394–407; Angelastro et al., *J. Med. Chem.* 1990, 33, 11–13) and tricarbonyl compounds (Wasserman et al., *J. Org. Chem.* 1993, 58, 4785–4787).

On the other hand, only one possibly specific inhibitor of oleamide hydrolase has been reported ($IC_{50}$=3 μM at [S]= 0.26 $K_m$) (Maurelli et al., *FEBS Lett.* 1995, 377, 82–86) and only one report of an investigation of inhibitors of related fatty acid amidases has been disclosed to date (Koutek et al., *J. Biol. Chem.* 1994, 269, 22937–22940).

What is needed are highly potent inhibitors of oleamide hydrolase for inhibiting the hydrolysis of oleamide and agonists of oleamide induced sleep.

BRIEF SUMMARY OF THE INVENTION

One aspect of the invention is directed to inhibitors of oleamide hydrolase. The inhibitors are designed to interact with active site cysteine residues within the oleamide hydrolase. The inhibitors are rapid, selective and highly potent ($K_i$=13 μM to 1 nM). The inhibitors are useful for inhibiting the hydrolysis of oleamide, a sleep inducing factor. The inhibitors are also useful tools for further characterizing the biological role of oleamide.

The inhibitors are of a type which include a head group and a hydrocarbon tail. The head group is covalently linked to the hydrocarbon tail and includes electrophilic carbonyl. Preferred head groups may be selected from a group consisting of radicals represented by the following structures:

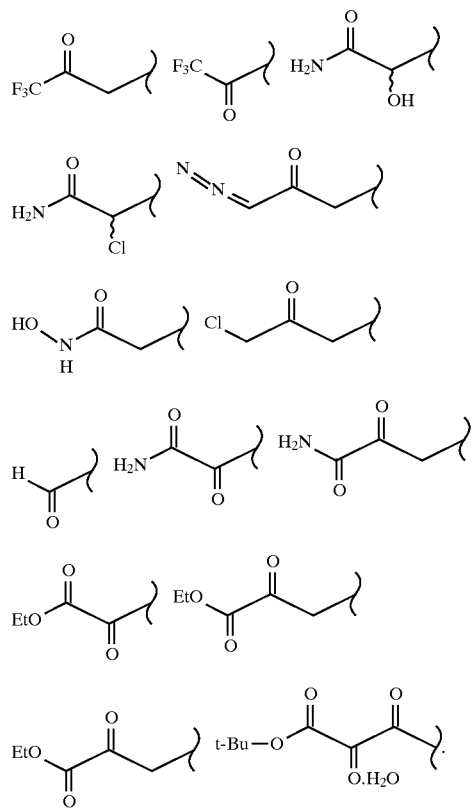

Preferred hydrocarbon tails may be selected from a group consisting of radicals represented by the following structures:

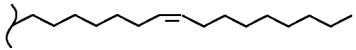

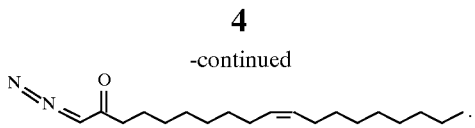

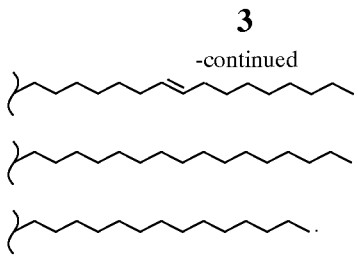

Preferred inhibitors include the following:

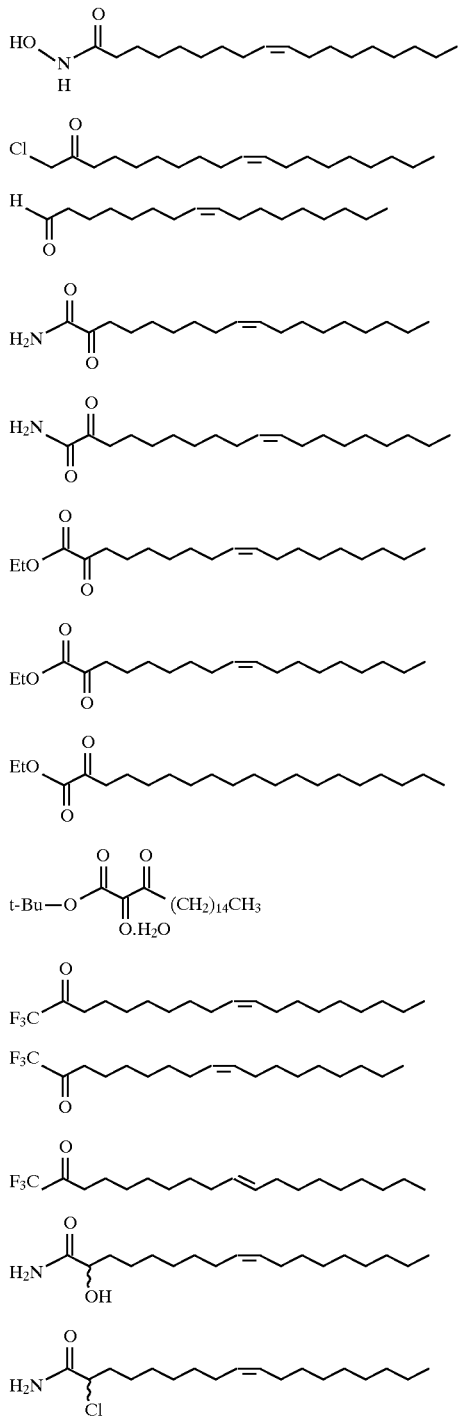

Another aspect of the invention is directed to a method for inhibiting oleamide hydrolyase with respect to the hydrolysis of oleamide. The method employs the act of contacting or combining the oleamide hydrolase with an inhibitor. The inhibitor is of a type having a head group and a hydrocarbon tail covalently linked thereto. The head group includes an electrophilic carbonyl group. Preferred head groups may be selected from a group consisting of radicals represented by the following structures:

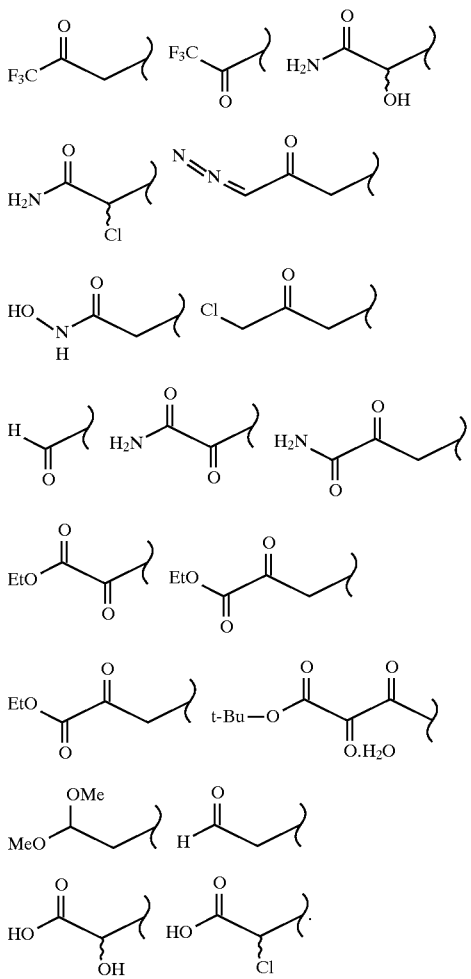

Preferred hydrocarbon tails may be selected from a group consisting of radicals represented by the following structures:

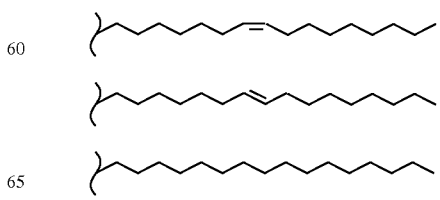

-continued

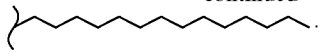

Preferred inhibitors employed in the above method include the inhibitors enumerated above and the following additional inhibitors:

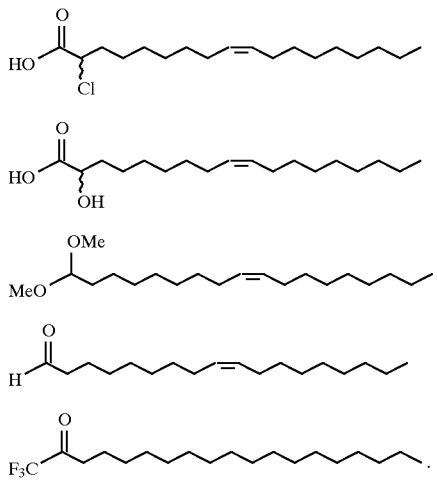

Another aspect of the invention is directed to a method for inducing sleep within an oleamide sensitive animal. More particularly, this aspect of the invention is directed to the administration to an oleamide sensitive animal of an effective dose of an agonist of oleamide hydrolase. A preferred agonist is represented by the following structure:

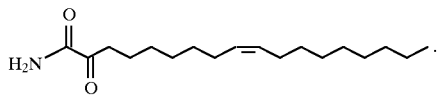

BRIEF DESCRIPTION OF DRAWINGS

FIG. 1 illustrates 22 inhibitors of oleamide hydrolase with respective inhibition constants ($K_{i,app}$ ($\mu$M); $K_m$=5±2 $\mu$M for oleamide.

FIG. 2 illustrates $^1$H NMR and $^{13}$C NMR data to establish and quantitate the addition of $CD_3OD$ or $D_2O$ to the electrophilic carbonyl in $CD_3OD$ or acetone-$d_6$. The data shows the extent of hydration and the relative electrophilic character of the inhibitor carbonyls. Expected trends follow 11>12>8>6≧4. Representative of these trends, 11 and 12 were fully converted to their hemiacetals in $CD_3OD$, and the remaining agents showed diminished hemiacetal formation consistent with their expected electrophilic character: 11(100%), 12(100%), 8(75%), 6(48%), and 4(47%).

FIG. 12 illustrates the equations used to determine the pH-Rate dependence. The rate was obtained from the linear portion of the curve which was fit using a standard least squares procedure. These rates were replotted against pH and fit with the shown equation by a weighted non-linear least-squares method.

DETAILED DESCRIPTION OF THE INVENTION

A series of potent transition-state-mimetic and mechanism-based oleamide hydrolase inhibitors 2–22 (FIGS. 1–2; 9, 10 and 11) are disclosed and characterized herein. These inhibitors are employable for exploring and defining the roles of 1 (FIG. 1) as a prototypical member of a new class of biological signaling agents and oleamide hydrolase as a potentially important factor in its regulation.

Figure 3:
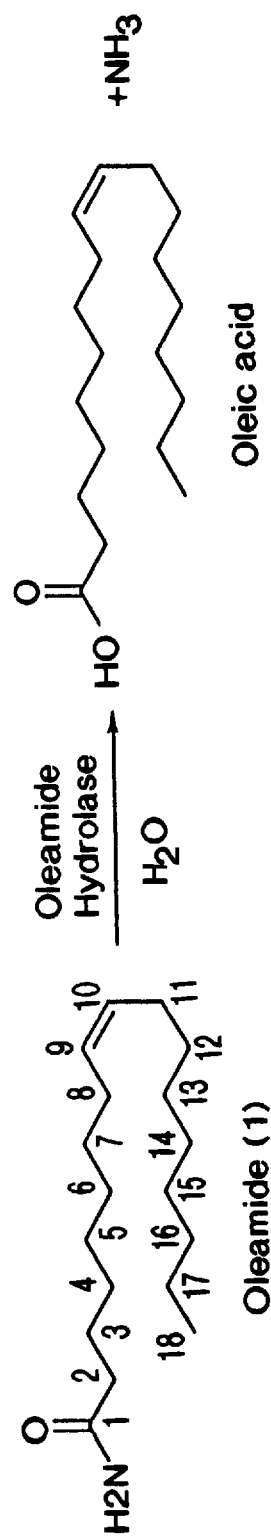
FIG. 3 illustrates the hydrolytic degradation of oleamide by oleamide hydrolase to give oleic acid (cis-9-octadecenoic acid) and ammonia.
Figure 4:
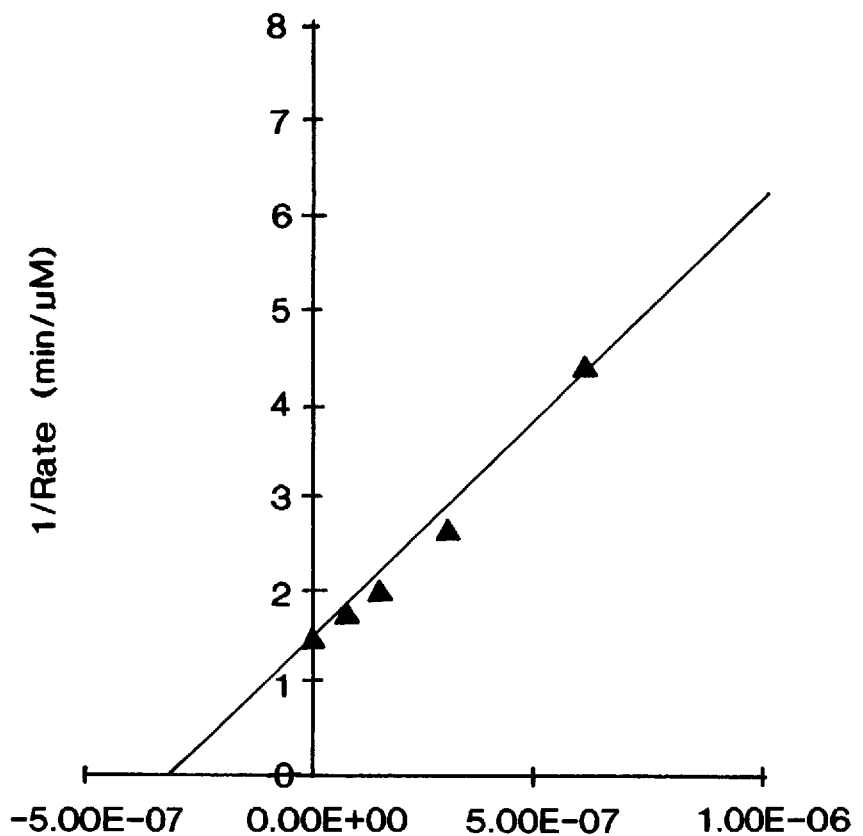
FIG. 4 illustrates a dixon plot of the activity of compound 6 (Molar) against oleamide hydrolase catalyzed degradation of oleamide 1 (1/Rate (min/$\mu$M)).
Figure 5:
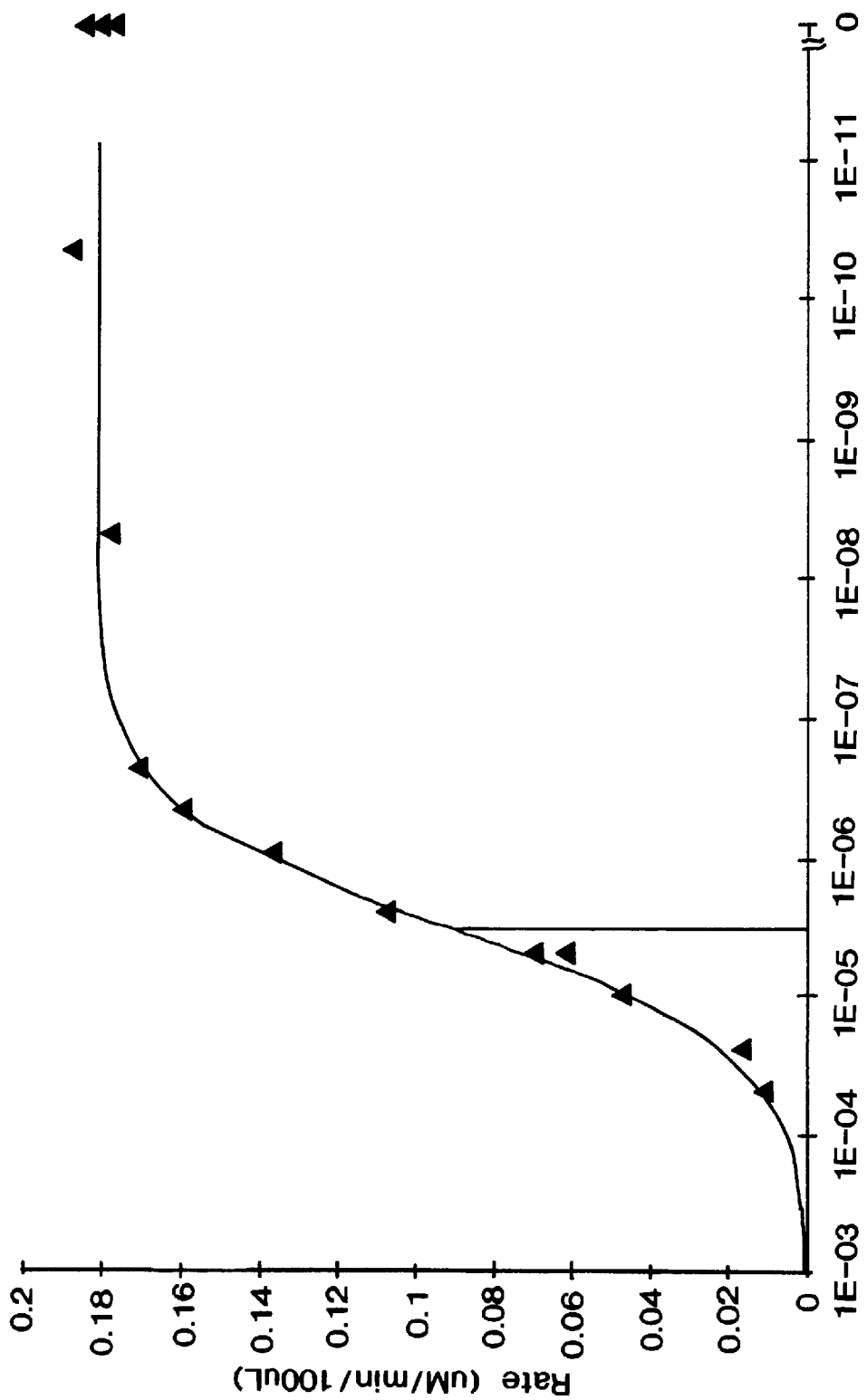
FIG. 5 illustrates the effect of compound 11 (Molar) against oleamide hydrolase (Rate ($\mu$M/min/100 $\mu$L)).
Figure 6:
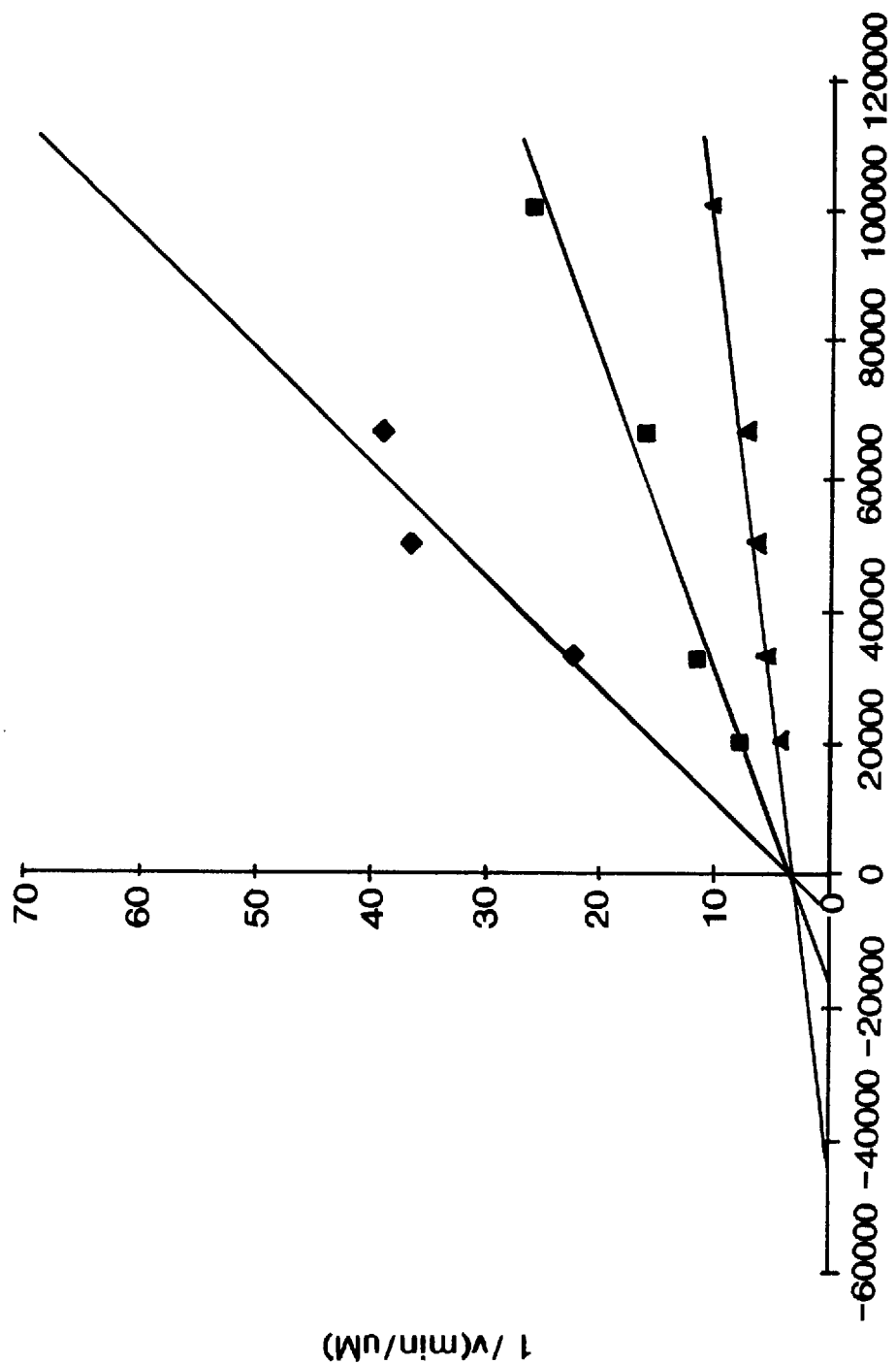
FIG. 6 illustrates a Lineweaver-Burke plot of competitive oleamide hydrolase inhibition (1/v(min/$\mu$M) by compound 12.

The potency of the inhibitors was determined using an ion selective electrode to measure the production of ammonia as the result of the hydrolysis of 100 $\mu$M oleamide (~20 $K_m$) by a membrane bound preparation of oleamide hydrolase. The $K_m$ of oleamide was found to be 5±2 $\mu$M. Inhibition constants were determined by the Dixon method (FIGS. 4–6). Subject to solubility limitations, all inhibitors that were tested were able to achieve 100% inhibition at high concentrations and no inhibitor exhibited polymodal inhibition behavior characteristic of two or more separate active sites with different $K_i$s. Since the likelihood of two or more different enzymes binding twenty-two separate inhibitors with nearly identical affinity is remote, this strongly suggests that a single enzyme in the preparation is responsible for greater than 90% of the observed oleamide hydrolase activity.

Figure 8:
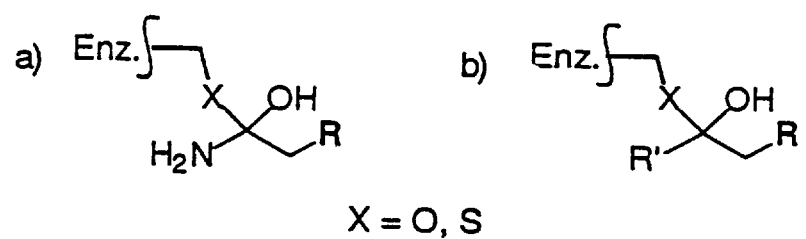
FIG. 8 illustrates in a) A common intermediate found in papain and other cysteine or serine proteases (O'Leary et al., Biochemistry 1974, 13, 2077–2081); b) The possible mode of action for inhibitors 3–15.

The most potent inhibitors (FIG. 1) possess an electrophilic carbonyl group capable of reversibly forming a (thio) hemiacetal or (thio) hemiketal to mimic the transition state of a serine or cysteine protease catalyzed reaction (FIG. 8). The relative potencies of the inhibitors were found to follow the expected electrophilic character of the reactive carbonyl cumulating in the tight binding α-keto ethyl ester 8 (1.4 nM) and the trifluoromethyl ketone inhibitor 12 (1.2 nM). A similar correlation between carbonyl electrophilicity and binding constant has been observed in inhibitors of insect juvenile hormone esterase (Linderman et al., Rev. Pestic. Toxicol. 1991, 1, 261–9) and anandaminase (Koutek et al., J. Biol. Chem. 1994, 269, 22937–22940). However, the most electrophilic member of the set, the tricarbonyl inhibitor 11 bound relatively poorly at 150 nM. This behavior may be the result of destabilizing stearic interactions between the bulky tert-butyl ester and the enzyme or may be in part due to the sp$^2$ character at C-3, which is uncharacteristic of the natural substrate.

The extent of hydration and the relative electrophilic character of the inhibitor carbonyls could be easily and accurately assessed by NMR analysis and they were found to follow the expected trends (e.g. 11>12>8>6≧4). The central carbonyl of the tricarbonyl inhibitor 11 was fully hydrated upon preparation and characterization. The remaining agents were isolated and characterized as their carbonyl structures without hydration including the reactive trifluoromethylketones. $^1$H NMR and $^{13}$C NMR were used to establish and quantitate the addition of $CD_3OD$ or $D_2O$ to the electrophilic carbonyl in $CD_3OD$ and acetone-$d_6$, respectively (FIG. 2). Representative of these trends, 11 and 12 were fully converted to their hemiacetals in $CD_3OD$, and the remaining agents showed diminished hemiacetal formation consistent with their expected electrophilic character: 11 (100%), 12 (100%), 8 (75%), 6 (48%), and 4 (47%).

While the trifluoromethyl ketones 12, 13, 14 and 15 exist in aqueous solution almost entirely as hydrates, these compounds are thought to bind to the enzyme as reversible covalent enzyme-inhibitor hemiketal complexes as shown in structural studies of elastase (Takahasi et al., *J. Mol. Biol.* 1988, 201, 423–428) and α-chymotrypsin (Liang et al., *Biochemistry* 1987, 26, 7603–7608) and kinetic studies of a series of serine proteases (Imperiali et al., *Biochemistry* 1986, 25, 3760–3767) bound to peptidyl trifluoromethyl ketones. Also, though the α-keto amides 6 and 7 are likely to exist at least in part as the $sp^2$ keto-species in solution, α-keto amides have been observed in protease active sites to be completely $sp^3$. Similarly, aldehydes in the active site of the cysteine protease papain bind as thiohemiacetals (Mackenzie et al., *Biochemistry* 1986, 25, 2293–2298; Schultz et al., *FEBS Lett.* 1975, 50, 47–49). The hypothesis that these inhibitors bind as (thio)-hemiketals rather than gem-diols (hydrated ketones) is further supported by the poor inhibition of oleamide hydrolase by 16, 17 and 18, despite their structural similarity to the gem-diol. We note that though electrophilicity of the reactive carbonyl seems to play a large role in dictating the affinity with which these inhibitors bind to oleamide hydrolase, there are likely other factors which also exert influence on the affinity of these compounds for oleamide hydrolase. While the aldehydes 4 and α-keto amide 7 appear to be equally electrophilic, the α-keto amide binds more tightly, suggesting that there are additional favorable interactions being made between the enzyme and the amide functionality, possibly an additional hydrogen bond(s). Similarly, the α-keto ester 8 and the trifluoromethyl ketone 12 bind equally tightly despite the the higher electrophilicity of the trifluoromethyl ketone.

Interestingly, aldehyde 5 which incorporates a carbonyl at a position analogous to C-2 of oleamide was found to bind five times more tightly than 4, which incorporates the aldehyde carbonyl in the position analogous to the C-1 of oleamide. This was also observed with the α-keto ester series of inhibitors, where the incorporation of the electrophilic carbonyl at C-2 versus C-1 of oleamide (8 versus 9) resulted in a 6-fold increase in binding affinity. This distinction was not seen in the α-keto amides or trifluoromethyl ketones. In these inhibitor classes the placement of the electrophilic carbonyl at the C-2 versus C-1 of oleamide position provided equally effective inhibitors. This suggests the possibility of subtly different binding modes for carbonyl positional analogs of C-1 versus C-2 of oleamide.

These studies also reveal that oleamide hydrolase displays an approximately ten-fold preference for fatty acid inhibitors which contain a cis double bond stereochemistry at the 9 position similar to the natural substrate. This trend is seen most clearly in the trifluoromethyl ketone series where cis double bond containing 12 is bound approximately an order of magnitude more tightly than the trans double bond containing 14 or the saturated derivative 15.

Most of the potential irreversible inhibitors (3, 19–21) demonstrated no measurable time dependent inhibitory activity over the first fifteen minutes of incubation at concentrations up to their solubility limits. The chloromethyl ketone 3 gave time independent but moderate inhibition ($K_i$=0.7 μM) which is consistent with the formation of a reversible (thio) hemiketal between the putative active site cysteine and the ketone (Bell et al., *Advan. Phys. Org. Chem.* 1966, 4, 1–29 and references therein) or a reversible and non-covalent enzyme-inhibitor complex. The presence of an adjacent chloro substituent augments the electrophilicity of the carbonyl, favoring nucleophilic attack. 2-Chlorooleic acid (20, $K_i$=0.3 μM) also appeared to bind reversibly, with its binding mode possibly similar to oleic acid ($K_i$=6 μM). Diazomethylketone 21 bound more weakly ($K_i$=18 μM).

Such observations suggest 1 may constitute a prototypical member of a class of fatty acid primary amide biological signaling molecules in which the diversity and selectivity of function is derived from the length of the alkane chain as well as the position, stereochemistry and degree of unsaturation.

Figure 7:
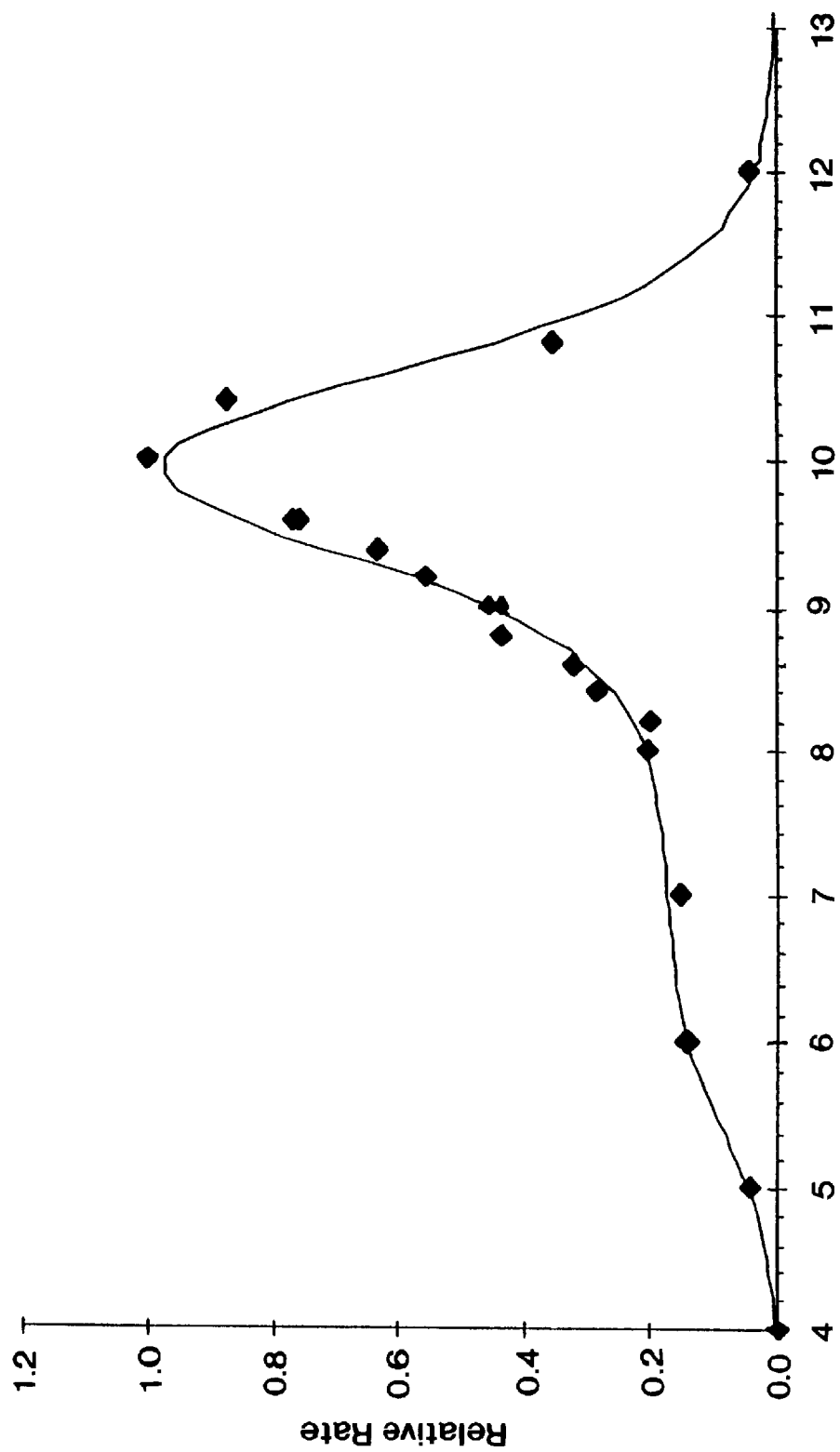
FIG. 7 illustrates the pH-rate dependence of oleamide hydrolase cleavage of compound 1 plot of relative rate against pH, with fit showing apparent active site pKa's of 5.4, 9.7, and 10.3. Rate maximum occurs at pH 10.0.

The rate of enzyme catalyzed oleamide hydrolysis was found to be pH dependent (FIG. 7) with apparent active site $pK_a$s of 5.4, 9.7 and 10.3. The unusual pH-rate dependence profile, oleamide $K_m$ and inhibition results for PMSF are consistent with results by Maurelli (Maurelli et al., *FEBS Lett.* 1995, 377, 82–86; Mackenzi et al., *Biochemistry* 1986, 25, 2293–2298), suggesting that the oleamide hydrolase presented here (from rat liver membrane fractions) and the anandamide amidohydrolase (from mouse neuroblastoma cell culture membrane fractions) may be the same enzyme, subject to inter-species variation. However, in the absence of sequence data or purified enzyme, the latter of which is often difficult to achieve with integral membrane proteins, this remains to be proven. However, our results are quite different from another report of anandamide amidohydrolase activity which exhibits rate maxima at pH 6 and 8 (Desarnaud et al., *J. Biol. Chem.* 1995, 270, 6030–6035) so there is also evidence to support a many-enzyme model of fatty acid amide hydrolysis in vivo. The inhibitors were assayed at pH 10.0, the pH at which oleamide hydrolase activity is at its maximum under our assay conditions.

Agonist Activity

Another aspect of the invention is directed to a method for inducing sleep within an oleamide sensitive animal by administrating an effective dose of an agonist of oleamide hydrolase. A preferred agonist is compound 6. Compound 6 was dissolved in mineral oil and an effective dose was injected into the peritoneum of a rat by intra-abdominal injection. Sleep was monitored for the following four hours. Total sleep time was determined by standard electrophysiological methods. An increase of deep slow-wave sleep (SWS) with a reduction of the waking period was observed. An increase of SWS of approximately 30% and a similar percent of reduction of waking was observed.

Inhibitor Synthesis

Figure 9A:
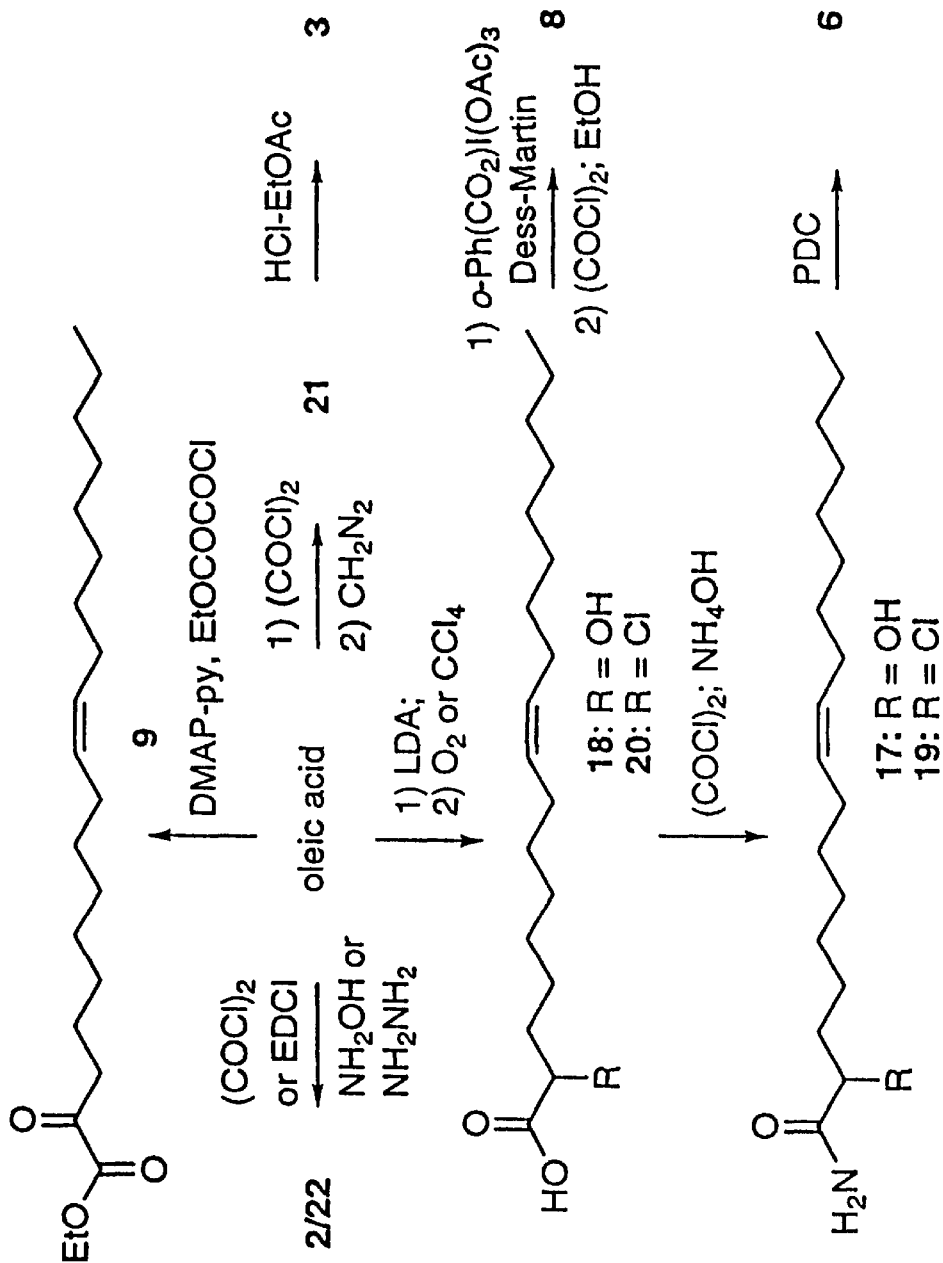
FIG. 9 illustrates the chemical synthesis of intermediates and inhibitors 3, 6, 7, 8, 10, 24, and 26.
Figure 9B:
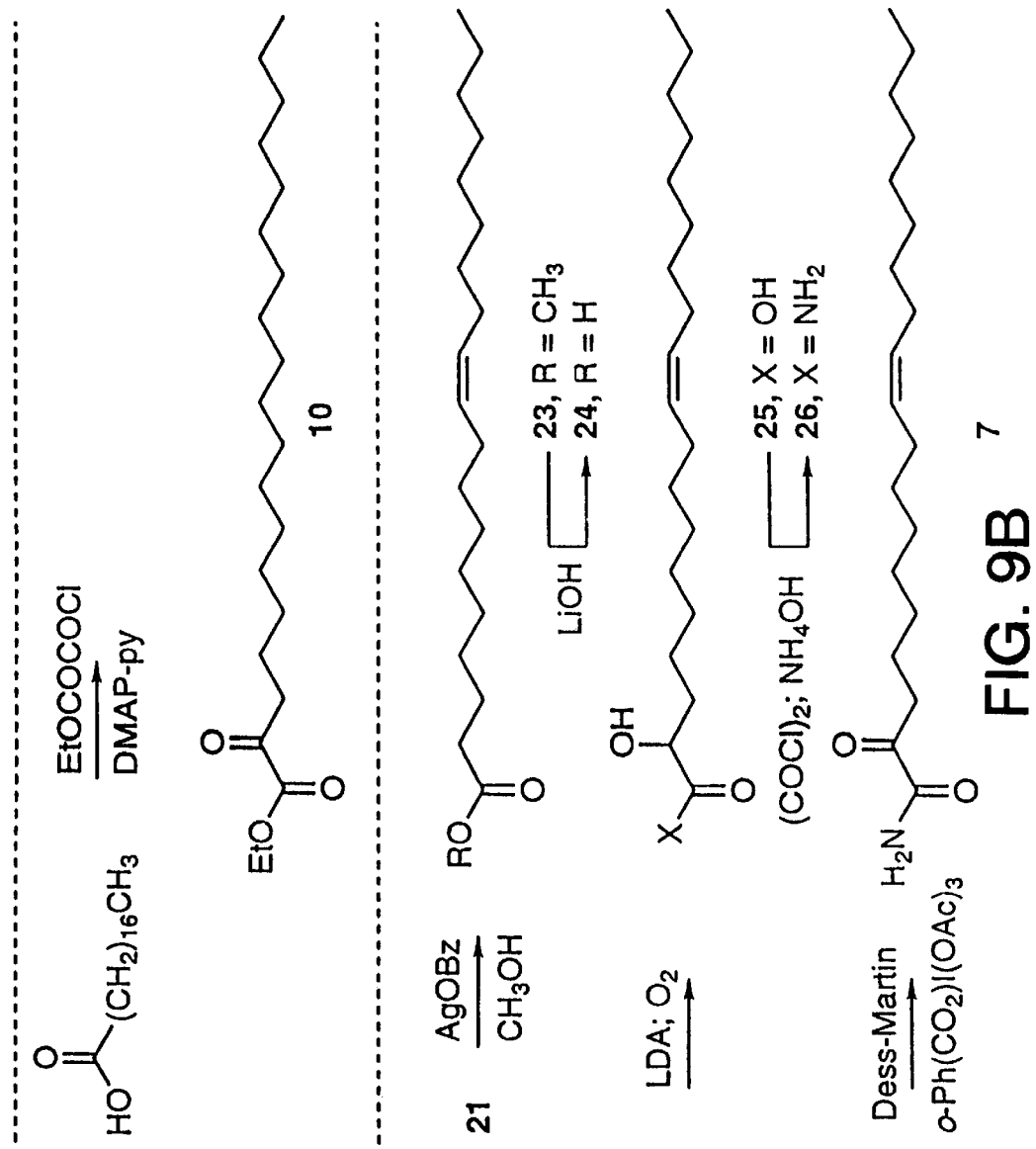

Many of the inhibitors were prepared from oleic acid by known procedures or adaption of known procedures (FIG. 9). Reaction of the acid chloride derived from oleic acid (3 equivalents $(COCl)_2$, $CH_2Cl_2$, 25° C., 3 hours) with hydroxylamine or diazomethane provided 2 and 21 and direct condensation of oleic acid with hydrazine (1.1 equivalents, 2.2 equivalents EDCI, 0.2 equivalent DMAP, $CH_2Cl_2$, 25° C., 19 hours) provided 22. Treatment of 21 with anhydrous 1N HCl-EtOAc (25° C., 10 minutes, 92%) cleanly provided 3. The aldehyde 4 (Mancuso et al., *J. Org. Chem.* 1978, 43, 2480–2482) along with the dimethyl acetal 16 (Marx et al., *J. Med. Chem.* 1989, 32, 1319–1322) could be prepared directly from oleic acid as described. Trap of the enolate derived from oleic acid (LDA, THF) with $CCl_4$ or $O_2$ provided 20 (Snider et al., *J. Org. Chem.* 1987, 52, 307–310) and 18 (Konen et al., *J. Org. Chem.* 1975, 40, 3253–3258) respectively, which were converted to the corresponding primary amides 19 and 17 via acid chloride generation (3 equivalents $(COCl)_2$, $CH_2Cl_2$, 25° C., 3 hours) and condensation with aqueous $NH_4OH$.

The C-18 oleic acid based α-ketoamide 6 and α-ketoester 8 bearing an electrophilic carbonyl at the position analogous to C-2 of oleamide rather than C-1 were prepared by oxidation of the α-hydroxyamide 17 (PDC) and α-hydroxy acid 18 (Dess-Martin) followed by ethyl ester formation (FIG. 9). The corresponding α-ketoesters 9 and 10, bearing an electrophilic carbonyl at the position analogous to C-1 of oleamide were prepared directly from the corresponding eighteen carbon carboxylic acids, oleic and stearic acids, employing a modified Dakin-West reaction (Buchanan et al., *Chem. Soc. Rev.* 1988, 17, 91–109)(FIG. 9). The a-ketoamide 7 of similar length was prepared by one carbon extension of oleic acid available through Wolff rearrangement of 21 (cat. AgOBz, CH3OH, 25° C., 2.5 hours, 82%) to provide the methyl ester 23. Hydrolysis of the methyl ester followed by conversion of the C-19 carboxylic acid 24 to the α-ketoamide followed the approach detailed for 6 (FIG. 9).

Figure 10:
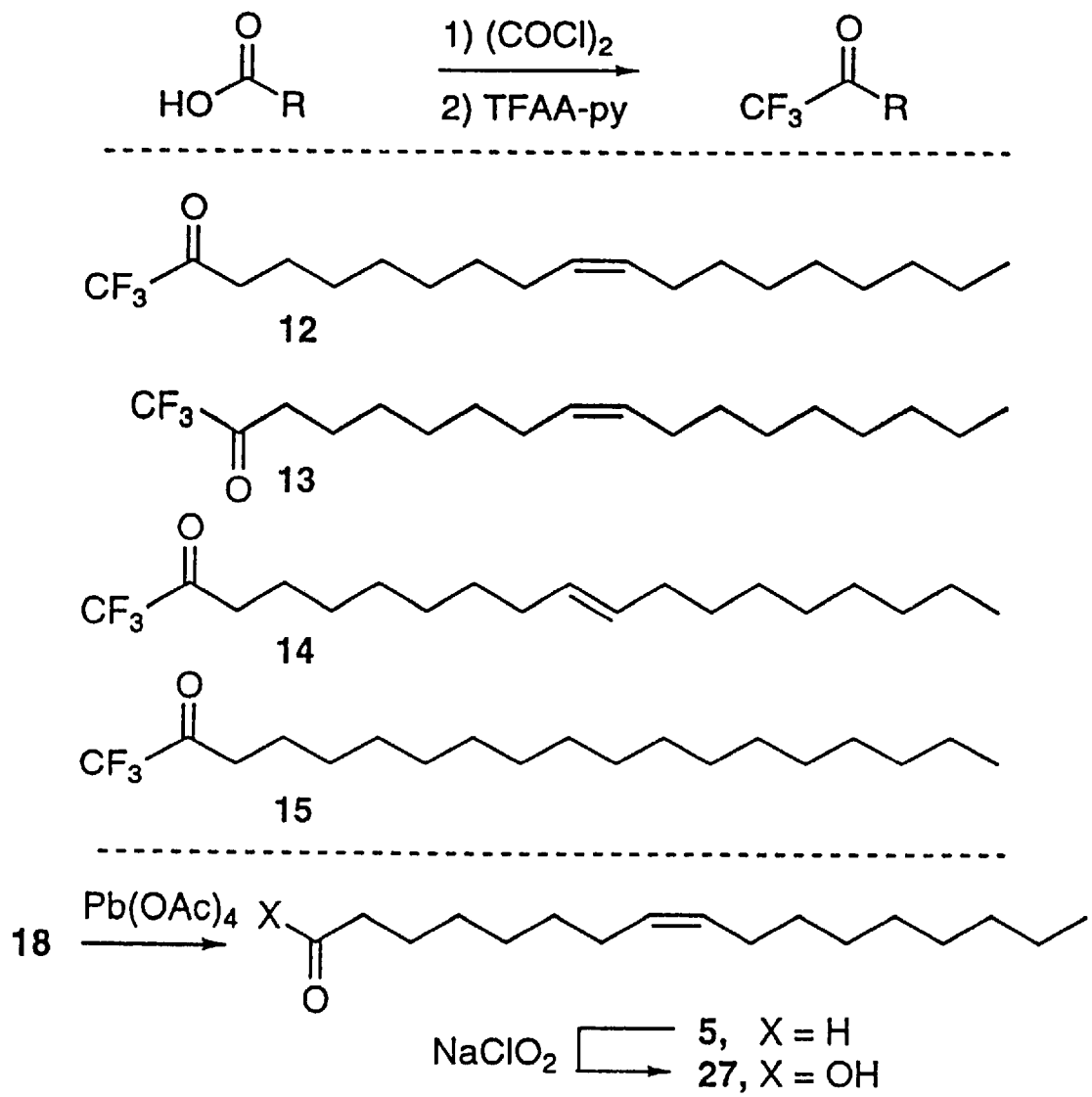
FIG. 10 illustrates the chemical synthesis of compound 27 from α-hydroxy acid 18 and shows trifluoromethyl ketone inhibitors 12, 13, 14, and 15 where R=$C_{16}H_{32}$-mono-unsaturated hydrocarbon as shown in FIG. 1.

The trifluoromethyl ketone inhibitors 12, 13, 14, and 15 including 13 which incorporates the electrophilic carbonyl at the C-2 position of a C-18 lipid containing a 9-cis olefin were prepared in one operation by conversion of the corresponding carboxylic acids to their respective acid chlorides and subsequent treatment with TFAA-pyridine (Boivin et al., *Tetrahedron Lett.* 1992, 33, 1285–1288) (6 equivalents/8 equivalents, $Et_2O$, 0.75–2 hours, 54–79%), (FIG. 10). Oxidative cleavage of a-hydroxy acid 18 ($Pb(OAc)_4$, 1.1 equivalents, 25° C., benzene, 50 m.) yielded aldehyde 5. This was further oxidized ($NaClO_2$) to give acid 27 which was used to prepare 13.

Figure 11:
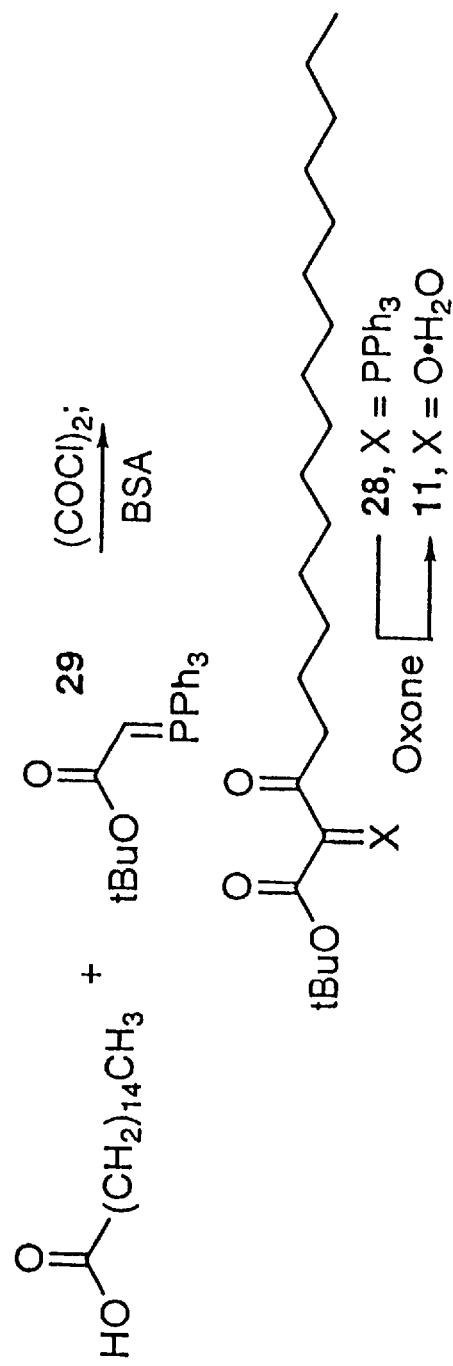
FIG. 11 illustrates the chemical synthesis of hydrated-saturated compound 11.

The tricarbonyl inhibitor 11 was prepared following the procedures detailed by Wasserman (Wasserman et al., *Tetrahedron Lett.* 1992, 33, 6003–6006). Treatment of the acid chloride derived from palmitic acid with tert-butyl (triphenylphosphoranylidene)acetate (29) in the presence of bis(trimethylsilyl)acetamide (BSA) followed by oxone oxidation provided 11 (FIG. 11).

Potent inhibitors of the enzyme oleamide hydrolase, responsible for the hydrolysis of an endogenous sleep-inducing lipid (1, cis-9-octadecenamide), have been developed, providing insights into the mechanism of the enzyme and the fundamental basis for the development of agents for the control and regulation of sleep.

SYNTHETIC PROTOCOLS

General

Optical rotations were measured on Perkin-Elmer 241 spectrophotometer UV and visible spectra were recorded on a Beckmann DU-70 spectrometer. $^1H$ and $^{13}C$ NMR spectra were recorded at 400 and 500 MHZ on Bruker AMX-400 and AMX-500 spectrometer. High-resolution mass spectra (HRMS) were recorded on a VG ZAB-ZSE mass spectrometer under fast atom bombardment (FAB) conditions. Column chromatography was carried out with silica gel of 70–230 mesh. Preparative TLC was carried out on Merck Art. 5744 (0.5 mm).

Synthesis of Compound 1

Compound 1 was prepared via procedures from Cravatt et al., *Science* 1995, 268, 1506–1509.

Synthesis of Compound 4

Compound 4 was prepared via procedures from Mancuso, A. J et al., *J. Org. Chem.* 1978, 43, 2480–2482

Synthesis of Compound 15

Compound 15 was prepared via procedures from Koutek, B. et al., *J. Biol. Chem.* 1994, 269, 22937–22940.

Synthesis of Compound 16 was prepared via procedures from Marx, M. H et al., *J. Med. Chem.* 1989, 32, 1319–1322.

Synthesis of Compound 18

Compound 18 was prepared via procedures from Konen et al., *J. Org. Chem.* 1975, 40, 3253–3258.

Synthesis of Compound 20

Compound 20 was prepared via procedures from Snider et al., *J. Org. Chem.* 1987, 52, 307–310.

Synthesis of Compound 29

Compound 29 was prepared via procedures from Cooke et al., *J. Org. Chem.* 1982, 47, 4955–4963.

Synthesis of N-Hydroxy-9Z-octadecenamide (2)

Oleic acid (250 μL, 0.79 mmol, 1 equivalent) was dissolved in anhydrous $CH_2Cl_2$ (4 mL) and cooled to 0° C. under $N_2$. Oxalyl chloride (2M in $CH_2Cl_2$, 1.2 mL, 2.4 mmol, 3 equivalents) was added slowly. The solution was warmed to 25° C. and allowed to stir for 3 hours in the dark. The solvent was removed in vacuo and the flask cooled to 0° C. Excess hydroxylamine in EtOAc (the hydrochloride salt was extracted into EtOAc from a 50% NaOH solution before use) was added slowly. The solvent was removed in vacuo and chromatography ($SiO_2$, 1.5×13 cm, 33–66% EtOAc-hexane gradient elution) afforded N-Hydroxy-9Z-octadecenamide 2 as a white solid (104 mg, 45%): mp 61°–62° C.; $^1H$ NMR ($CD_3OD$, 400 MHZ) δ 5.28–5.20 (m, 2H), 2.00–1.91 (m, 6H), 1.50 (p, 2H, J=6.8 Hz), 1.22–1.19 (m, 20H), 0.80 (t, 3H, J=6.9 Hz); $^{13}C$ NMR ($CD_3OD$, 100 MHZ) δ 173.0, 130.9, 130.8, 33.8, 33.1, 30.9(2), 30.6, 30.5, 30.4, 30.33(2), 30.26, 30.19, 28.2, 26.8, 23.8, 14.5; IR (film) $v_{max}$ 3276, 2999, 2917, 2849, 1665, 1621, 1463, 1428, 1117, 1067, 968 $cm^{-1}$; FABHRMS (NBA-NaI) m/z 320.2577 ($C_{18}H_{35}NO_2+Na^+$ requires 320.2565).

Synthesis of 1-Chloro-10Z-nonadecen-2-one (3)

A sample of 21 (347 mg, 1.13 mmol, 1 equivalent) was treated with 1M HCl in EtOAc (4.0 mL, 4.0 mmol, 3.5 equivalents) for 10 minutes at 25° C. before the mixture was concentrated in vacuo. Chromatography ($SiO_2$, 3×13 cm, 5% EtOAc-hexane) afforded 3 (328 mg, 92%) as a clear oil: $^1H$ NMR ($CD_3OD$, 400 MHZ) δ 5.29–5.21 (m, 2H), 4.18 (s, 2H), 2.48 (t, 2H, J=7.3 Hz), 1.93 (m, 4H), 1.50 (p, 2H, J=7.1 Hz), 1.31–1.21 (m, 20H), 0.81 (t, 3H, J=6.8 Hz); $^{13}C$ NMR ($CD_3OD$, 100 MHZ δ 204.5, 130.9, 130.8, 49.3, 40.3, 33.1, 30.9, 30.8, 30.6, 30.5, 30.40, 30.37, 30.19, 30.17(2), 28.1, 24.6, 23.8, 14.5; IR (film) $v_{max}$ 2925, 2854, 1722, 1463, 1403, 1260, 1101, 796, 723 $cm^{-1}$; FABHRMS (NBA) m/z 315.2468 ($C_{19}H_{35}OCl+H^+$ requires 315.2455).

Synthesis of 8Z-Heptadecenal (5)

A solution of 18 (120 mg, 0.40 mmol, 1 equivalent) in anhydrous benzene (1.6 mL) at 25° C. under $N_2$ was treated with $Pb(OAc)_4$ (197 mg, 0.44 mmol, 1.1 equivalents) and the reaction mixture was stirred for 50 minutes. Water (2 mL) was added and the aqueous layer was extracted with EtOAc (6×2 mL). The organic layers were dried ($Na_2SO_4$), filtered, and concentrated in vacuo. Chromatography ($SiO_2$, 2×13 cm, 1–5% EtOAc-hexane gradient elution) afforded 5 (68 mg, 67%) as a clear oil. Spectral properties agree with those described in the literature (Doleshall et al., *Tetrahedron Lett.* 1977, 381–382; Kemp et al., *J. Am. Oil Chem. Soc.* 1975, 52, 300–302).

Synthesis of 2-Oxo-9Z-octadecenamide (6).

A solution of 17 (8 mg, 0.027 mmol, 1 equivalent) in anhydrous DMF (0.13 mL) under Ar was treated with PDC (51 mg, 0.13 mmol, 5 equivalents) and the reaction mixture was stirred for 1 hour at 25° C. The crude reaction was treated with $H_2O$ (2 mL) and the aqueous layer was extracted with $Et_2O$ (4×2 mL). The organic layers were dried ($Na_2SO_4$), filtered, and concentrated in vacuo. Chromatography ($SiO_2$, 1×3 cm, 20–66% EtOAc-hexane gradient elution) afforded 6 (6 mg, 70%) as a white solid and some recovered starting material (2 mg, 26%). For 6: mp 85°–86° C.; $^1$H NMR ($CDCl_3$, 400 MHZ) δ 6.79 (br, 1H), 5.47 (br, 1H), 5.37–5.28 (m, 2H), 2.89 (t, 2H, J=7.4 Hz), 2.02–1.93 (m, 4H), 1.59 (p, 2H, J=7.2 Hz), 1.39–1.24 (m, 20H), 0.86 (t, 3H, J=6.8 Hz); $^{13}$C NMR ($CDCl_3$, 100 MHZ) δ 198.6, 161.9, 130.1, 129.6, 36.5, 31.9, 29.7, 29.5(2), 29.3(2), 28.9(2), 27.2, 27.1, 23.1, 22.7, 14.1; IR (film) $v_{max}$ 3391, 2915, 2850, 1716, 1668, 1470, 1400, 1108 $cm^{-1}$; FABHRMS (NBA-CsI) m/z 428.1547 ($C_{18}H_{33}NO_2$+$Cs^+$ requires 428.1566).

Synthesis of 2-Oxo-10Z-nonadecenamide (7)

A solution of 26 (42 mg, 0.14 mmol, 1 equivalent) in anhydrous $CH_2Cl_2$ (2.8 mL) at 25° C. was treated with o-Ph($CO_2$)I($OAc$)$_3$ (174 mg, 0.41 mmol, 3 equivalents) and the reaction mixture was stirred for 1.5 hours. The mixture was treated with 10% aqueous NaOH (30 mL) and the aqueous layer was extracted with EtOAc (3× 30 mL). The organic layers were dried ($Na_2SO_4$), filtered, and concentrated in vacuo. Chromatography ($SiO_2$, 1.5×13 cm, 10–20% EtOAc-hexane gradient elution) afforded 7 (24 mg, 57%) as a white solid: mp 69°–70° C.; $^1$H NMR ($CDCl_3$, 400 MHZ δ 6.82 (br, 1H), 5.68 (br, 1H), 5.36–5.28 (m, 2H), 2.88 (t, 2H, J=7.4 Hz), 1.98 (m, 4H), 1.58 (p, 2H, J=7.0 Hz), 1.28–1.24 (m, 20H), 0.85 (t, 3H, J=6.9 Hz); $^{13}$C NMR ($CDCl_3$, 100 MHZ δ 198.7, 162.0, 130.0, 129.7, 36.5, 31.9, 29.74, 29.66, 29.5, 29.3(2), 29.2, 29.1, 29.0, 27.2, 27.1, 23.1, 22.7, 14.1; IR (film) $v_{max}$ 3395, 3217, 2922, 2850, 1718, 1672, 1601, 1469, 1406, 1115 $cm^{-1}$; FABHRMS (NBA-NaI) m/z 332.2570 ($C_{19}H_{35}NO_2$+$Na^+$ requires 332.2565).

Synthesis of Ethyl 2-Oxo-9Z-octadecenoate (8)

A solution of 18 (102 mg, 0.34 mmol, 1 equivalent) in anhydrous $CH_2Cl_2$ (1.1 mL) at 25° C. under $N_2$ was treated with o-Ph($CO_2$)I($OAc$)$_3$ (287 mg, 0.68 mmol, 2 equivalents) and stirred for 1 hour. The reaction mixture was treated with 10% aqueous NaOH (20 mL) and extracted with EtOAc (3×20 mL). The organic layers were dried ($Na_2SO_4$), filtered, and concentrated in vacuo. The residue was dissolved in anhydrous $CH_2Cl_2$ (1.5 mL) and cooled to 0° C. under $N_2$. Oxalyl chloride (2M in $CH_2Cl_2$, 0.5 mL, 1.0 mmol, 3 equivalents) was added slowly. The reaction mixture was warmed to 25° C. and was stirred in the dark for 3 hours before the solvent was removed in vacuo and absolute EtOH (5 mL) was added. Chromatography ($SiO_2$, 2×10 cm, 1–5% EtOAc-hexane) afforded 8 (36 mg, 33%) as a clear oil: $^1$H NMR ($CDCl_3$, 400 MHZ) δ 5.37–5.27 (m, 2H), 4.29 (q, 2H, J=7.2 Hz), 2.81 (t, 2H, J=7.3 Hz), 1.98 (m, 4H), 1.61 (p, 2H, J=7.1 Hz), 1.36–1.24 (m, 21H), 0.86 (t, 3H, J=6.8 Hz); $^{13}$C NMR ($CDCl_3$, 100 MHZ δ 194.8, 161.3, 130.1, 129.6, 62.4, 39.3, 31.9, 29.8, 29.5(2), 29.3(2), 28.92, 28.86, 27.2, 27.1, 22.9, 22.7, 14.1, 14.0; IR (film) $v_{max}$ 2925, 2854, 1729, 1462, 1260, 1056 $cm^{-1}$; FABHRMS (NBA-CsI) m/z 457.1706 ($C_{20}H_{36}O_3$+$Cs^+$ $Cs^+$ requires 457.1719).

Synthesis of Ethyl 2-Oxo-10Z-nonadecenoate (9)

A solution of oleic acid (100 μL, 0.32 mmol, 1 equivalent) in anhydrous THF (0.2 mL) at 25° C. under Ar was treated with DMAP (4 mg, 0.03 mmol, 0.1 equivalent), anhydrous pyridine (77 μL, 0.95 mmol, 3 equivalents), and ethyl oxalyl chloride (71 μL, 0.64 mmol, 2 equivalents). The reaction mixture was stirred for 24 hours before additional DMAP (46 mg, 0.37 mmol, 1.1 equivalents), pyridine (80 μL, 0.95 mmol, 3 equivalents), ethyl oxalyl chloride (80 μL, 0.64 mmol, 2 equivalents), and THF (0.5 mL) were added. The reaction mixture was stirred at 25° C. for an additional 24 hours and then was warmed to 40° C. for 48 hours before the solvent was concentrated in vacuo. Chromatography ($SiO_2$, 2×13 cm, 0–10% EtOAc-hexane) afforded 9 (46 mg, 43%) as a clear oil: $^1$H NMR ($CDCl_3$, 400 MHZ) δ 5.36–5.28 (m, 2H), 4.29 (q, 2H, J=7.1 Hz), 2.80 (t, 2H, J=7.3 Hz), 1.99 (m, 4H), 1.60 (m, 2H), 1.36–1.20 (m, 23H), 0.85 (t, 3H, J=6.8 Hz); $^{13}$C NMR ($CDCl_3$, 100 MHZ δ 194.8, 161.2, 130.0, 129.7, 62.4, 39.3, 31.9, 29.7, 29.6, 29.5, 29.3(2), 29.2, 29.0, 28.9, 27.2, 27.1, 22.9, 22.7, 14.1, 14.0; IR (film) $v_{max}$ 2925, 2854, 1730, 1465, 1260, 1059 $cm^{-1}$; FABHRMS (NBA-CsI) m/z 471.1875 ($C_{21}H_{38}O_3$+$Cs^+$ requires 471.1888).

Synthesis of Ethyl 2-Oxo-nonadecanoate (10)

A solution of stearic acid (101 mg, 0.36 mmol, 1 equivalent) in anhydrous THF (0.2 mL) at 25° C. under Ar was treated with DMAP (4 mg, 0.03 mmol, 0.1 equivalent), anhydrous pyridine (85 μL, 1.1 mmol, 3 equivalents), and ethyl oxalyl chloride (79 μL, 0.71 mmol, 2 equivalents). The reaction mixture was stirred for 24 hours before the solvent was concentrated in vacuo. Chromatography ($SiO_2$, 2×13 cm, 5–10% EtOAc-hexane) afforded 10 (35 mg, 30%) as a white solid: mp 43°–44° C.; $^1$H NMR ($CDCl_3$, 400 MHZ δ 4.29 (q, 2H, J=7.2 Hz), 2.80 (t, 2H, J=7.4 Hz), 1.60 (p, 2H, J=7.2 Hz), 1.35 (t, 3H, J=7.1 Hz), 1.33–1.23 (m, 28H), 0.86 (t, 3H, J=6.8 Hz); $^{13}$C NMR ($CDCl_3$, 100 MHZ) δ 194.8, 161.2, 62.4, 39.3, 31.9, 29.7(7), 29.6, 29.40, 29.35, 29.28, 28.9, 23.0, 22.7, 14.1, 14.0; IR (film) $v_{max}$ 2916, 2848, 1733, 1472, 1463, 723 $cm^{-1}$; FABHRMS (NBA-NaI) m/z 363.2885 ($C_{21}H_{40}O_3$+$Na^+$ requires 363.2875).

Synthesis of tert-Butyl 3-Oxo-2,2-dihydroxyoctadecanoate (11)

A solution of 28 (161 mg, 0.26 mmol, 1 equivalent) in THF-$H_2O$ (2:1; 3 mL) was treated with Oxone (249 mg, 0.41 mmol, 1.6 equivalents) and the reaction mixture was stirred at 25° C. for 7 hours. Water (30 mL) was added and the aqueous layer was extracted with EtOAc (3×30 mL). The organic layers were combined, dried ($Na_2SO_4$), filtered, and concentrated in vacuo. Chromatography ($SiO_2$, 2×15 cm, 10–20% EtOAc-hexane gradient elution) afforded 11 (65 mg, 64%) as a white solid: mp 49°–51° C; $^1$H NMR (DMSO-$d_6$, 400 MHZ δ 6.96 (s, 2H), 2.17 (t, 2H, J=7.4 Hz), 1.49–1.38 (m, 11H), 1.22 (s, 24H), 0.84 (t, 3H, J=6.8 Hz); $^{13}$C NMR (DMSO-$d_6$, 100 MHZ δ 205.6, 174.5, 94.2, 81.5, 35.6, 33.6, 31.3, 29.0(3), 28.9, 28.8, 28.72, 28.70, 28.53, 28.46, 27.4(2), 24.5, 22.9, 22.1, 13.9; IR (film) $v_{max}$ 3440, 2914, 2849, 1728, 1471, 1371, 1260, 1122, 831, 718 $cm^{-1}$; FABHRMS (NBA-NaI) m/z 409.2925 ($C_{22}H_{42}O_5$+$Na^+$ requires 409.2930).

Synthesis of 1,1,1-Trifluoro-10Z-nonadecen-2-one (12)

Oleic acid (100 μL, 0.32 mmol, 1 equivalent) was dissolved in anhydrous $CH_2Cl_2$ (1.5 mL) and cooled to 0° C. under $N_2$. Oxalyl chloride (2M in $CH_2Cl_2$, 0.47 mL, 0.94 mmol, 3 equivalents) was added slowly. The reaction mixture was warmed to 25° C. and was stirred in the dark for 3 hours before the solvent was removed in vacuo. Anhydrous $Et_2O$ (2.2 mL), trifluoroacetic anhydride (270 μL, 1.9 mmol, 6 equivalents) and pyridine (0.2 mL, 2.5 mmol, 8 equivalents) were added at 25° C. and the solution was stirred for 45 minutes before being cooled to 0° C. The reaction was quenched with the addition of $H_2O$ (30 mL) and the aqueous layer was extracted with $CH_2Cl_2$ (3×30 mL). The organic layers were dried ($Na_2SO_4$), filtered, and concentrated in vacuo. Chromatography (SiO$_2$, 1.5×13 cm, 1% Et$_3$N in 5% EtOAc-hexane) afforded 8 (75 mg, 71%) as a clear oil: $^1$H NMR (CDCl$_3$, 400 MHZ) δ 5.37–5.28 (m, 2H), 2.68 (t, 2H, J=7.3 Hz), 1.98 (m, 4H), 1.65 (p, 2H, J=7.1 Hz), 1.29–1.25 (m, 20H), 0.86 (t, 3H, J=6.9 Hz); $^{13}$C NMR (CDCl$_3$, 100 MHZ) δ 191.6 (d, J=17 Hz), 130.0, 129.5, 115.6 (q, J=145 Hz), 36.3, 31.9, 29.8, 29.6, 29.5, 29.3(2), 29.1, 29.0, 28.7, 27.2, 27.1, 22.7, 22.4, 14.1; IR (film) $v_{max}$ 2926, 2855, 1766, 1467, 1404, 1261, 1208, 1153, 1039, 802, 709 cm$^{-1}$; ESIMS m/z M$^+$) 334.

Synthesis of 1,1,1-Trifluoro-9Z-octadecen-2-one (13)

A solution of 27 (101 mg, 0.38 mmol, 1 equivalent) in anhydrous CH$_2$Cl$_2$ (1.8 mL) was cooled to 0° C. under N$_2$ and treated dropwise with oxalyl chloride (2M in CH$_2$Cl$_2$, 0.56 mL, 1.1 mmol, 3 equivalents). The reaction mixture was warmed to 25° C. and stirred for 3 hours before the solvent was removed in vacuo. Anhydrous Et$_2$O (2.5 mL), trifluoroacetic anhydride (0.32 mL, 2.3 mmol, 6 equivalents), and anhydrous pyridine (0.12 mL, 1.5 mmol, 4 equivalents) were added at 25° C. and the solution was stirred for 2 hours before being cooled to 0° C. The reaction mixture was treated with H$_2$O (30 mL) and the aqueous layer was extracted with EtOAc (3×30 mL). The organic layers were dried (Na$_2$SO$_4$), filtered, and concentrated in vacuo. Chromatography (SiO$_2$, 2×15 cm, 1% Et$_3$N in 10% EtOAc-hexane) afforded 13 (65.5 mg, 54%) as a clear oil: $^1$H NMR (CDCl$_3$, 400 MHZ δ 5.39–5.26 (m, 2H), 2.69 (t, 2H, J=7.2 Hz), 1.99 (m, 4H), 1.66 (m, 2H), 1.35–1.24 (m, 18H), 0.86 (t, 3H, J=6.9 Hz); $^{13}$C NMR (CDCl$_3$, 100 MHZ δ 191.4, 130.5, 129.1, 115.6 (q, J=146 Hz), 36.3, 31.9, 29.7, 29.5, 29.3(3), 29.2, 28.3, 27.2, 26.8, 22.7, 22.3, 14.1; IR (film) $v_{max}$ 2926, 2855, 1765, 1462, 1209, 1154, 1024 cm$^{-1}$; ESIMS m/z (M+Na$^+$) 343.

Synthesis of 1,1,1-Trifluoro-10E-nonadecen-2-one (14)

A solution of elaidic acid (204 mg, 0.72 mmol, 1 equivalent) in anhydrous CH$_2$Cl$_2$ (3.5 mL) was cooled to 0° C. under N$_2$ and treated with oxalyl chloride (2M in CH$_2$Cl$_2$, 1.1 mL, 2.2 mmol, 3 equivalents). The reaction mixture was warmed to 25° C. and stirred for 3 hours before the solvent was removed in vacuo. Anhydrous Et$_2$O (5 mL), trifluoroacetic anhydride (0.6 mL, 4.3 mmol, 6 equivalents), and anhydrous pyridine (0.23 mL, 2.8 mmol, 4 equivalents) were added at 25° C. and the solution was stirred for 1 hour before being cooled to 0° C. The mixture was treated with H$_2$O (30 mL) and the aqueous layer was extracted with EtOAc (3×30 mL). The organic layers were dried (Na$_2$SO$_4$), filtered, and concentrated in vacuo. Chromatography (SiO$_2$, 2×13 cm, 1% Et$_3$N in 5–10% EtOAc-hexane gradient elution) afforded 14 (190 mg, 79%) as a clear oil: $^1$H NMR (CDCl$_3$, 400 MHZ) δ 5.41–5.31 (m, 2H), 2.68 (t, 2H, J=7.3 Hz), 1.94 (m, 4H), 1.65 (p, 2H, J=6.9 Hz), 1.28–1.24 (m, 20H), 0.86 (t, 3H, J=6.6 Hz); $^{13}$C NMR (CDCl$_3$, 100 MHZ) δ 191.5 (q, J=35 Hz), 130.6, 130.1, 115.6 (q, J=291 Hz), 36.3, 32.6, 32.5, 31.9, 29.7, 29.5(2), 29.3, 29.2, 29.1, 28.8, 28.7, 22.7, 22.4, 14.0; IR (film) $v_{max}$ 2925, 2855, 1765, 1466, 1208, 1152, 967, 709 cm$^{-1}$; FABHRMS (NBA-NaI) m/z 334.2475 (C$_{19}$H$_{33}$OF$_3$—H$^+$ requires 334.2484).

Synthesis of 2-Hydroxy-9Z-octadecenamide (17)

A solution of 18 (52 mg, 0.18 mnol, 1 equivalent) in anhydrous CH$_2$Cl$_2$ (0.7 mL) cooled to 0° C. under N$_2$ was treated with oxalyl chloride (2M in CH$_2$Cl$_2$, 0.22 mL, 0.44 mmol, 3 equivalents). The solution was allowed to warm to 25° C. and stirred for 3 hours in the dark. The solvent was removed in vacuo and the acid chloride was cooled to 0° C. The sample was treated with excess concentrated aqueous NH$_4$OH. Chromatography (SiO$_2$, 1.5×10 cm, 66–100% EtOAc-hexane gradient elution) afforded 17 (31 mg, 60%) as a white solid: mp 103°–104° C.; $^1$H NMR (CDCl$_3$, 400 MHZ) δ 6.37 (br, 1H), 5.64 (br, 1H), 5.36–5.28 (m, 2H), 4.12 (t, 1H, J=3.8 Hz), 2.66 (br, 1H), 2.02–1.94 (m, 4H), 1.86–1.77 (m, 1H), 1.68–1.59 (m, 1H), 1.43–1.24 (m, 20H), 0.86 (t, 3H, J=6.8 Hz); $^{13}$C NMR (CDCl$_3$, 100 MHZ) δ 176.6, 130.0, 129.7, 71.9, 34.8, 31.9, 29.7, 29.6, 29.5, 29.3(2), 29.2, 29.1, 27.2, 27.1, 24.9, 22.7, 14.1; IR (film) $v_{max}$ 3381, 3289, 2917, 2848, 1637, 1461, 1417, 1331, 1074 cm$^{-1}$; FABHRMS (NBA) m/z 298.2760 (C$_{18}$H$_{35}$NO$_2$+H$^+$ requires 298.2746).

Synthesis of 2-Chloro-9Z-octadecenamide (19)

A solution of 20 (48 mg, 0.15 mmol, 1 equivalent) in anhydrous CH$_2$Cl$_2$ (0.7 mL) cooled to 0° C. under N$_2$was treated with oxalyl chloride (2M in CH$_2$Cl$_2$, 0.23 mL, 0.46 mmol, 3 equivalents). The solution was allowed to warm to 25° C. and was stirred for 3 hours in the dark before the solvent was removed in vacuo. The crude acid chloride was cooled to 0° C. and treated with excess concentrated aqueous NH$_4$OH. Chromatography (SiO$_2$, 1.5×10 cm, 20–33% EtOAc-hexane gradient elution) afforded 19 (37 mg, 78%) as a yellow solid: mp 49°–50° C.; $^1$H NMR (CDCl$_3$, 400 MHZ) δ 6.49 (br, 1H), 5.92 (br, 1H), 5.36–5.27 (m, 2H), 4.29 (m, 1H), 2.12–1.86 (m, 6H), 1.53–1.16 (m, 20H), 0.85 (t, 3H, J=6.9 Hz); $^{13}$C NMR (CDCl$_3$, 100 MHZ) δ 171.9, 130.1, 129.6, 60.6, 35.5, 31.9, 29.7, 29.6, 29.5, 29.3(2), 29.0, 28.7, 27.2, 27.1, 25.8, 22.7, 14.1; IR (film) $v_{max}$ 3383, 3183, 3001, 2921, 2850, 1657, 1465, 1412, 1240, 1100 cm$^{-1}$; FABHRMS (NBA) m/z 316.2415 (C$_{18}$H$_{34}$NOCl+H$^+$ requires 316.2407).

Synthesis of 1-Diazo-10Z-nonadecen-2-one (21)

Oleic acid (1.0 mL, 3.2 mmol, 1 equivalent) was dissolved in anhydrous CH$_2$Cl$_2$ (15 mL) under N$_2$. The solution was cooled to 0° C. and oxalyl chloride (2M in CH$_2$Cl$_2$, 4.8 mL, 9.6 mmol, 3 equivalents) was added. The reaction mixture was allowed to warm to 25° C. and was stirred for 3 hours in the dark. The solvent was removed in vacuo before the acid chloride was transferred to a flask with no ground glass joints and cooled to 0° C. Excess diazomethane in Et$_2$O (prepared from N-nitrosomethylurea in 50% aqueous KOH and drying over KOH pellets) was added. The reaction was stirred at 0° C. for 1 hour before warming to 25° C. overnight. The solution was diluted with EtOAc (60 mL) and washed with saturated aqueous NaHCO$_3$(60 mL) and saturated aqueous NaCl (60 mL). The organic layer was dried (Na$_2$SO$_4$), filtered, and concentrated in vacuo. Chromatography (SiO$_2$, 4.0×16 cm, 5–10% EtOAc-hexane gradient elution) afforded 21 (0.89 g, 92%) as a yellow oil: $^1$H NMR (CD$_3$OD, 400 MHZ) δ 5.72 (br, 1H), 5.29–5.21 (m, 2H), 2.23 (m, 2H), 1.94 (m, 4H), 1.50 (p, 2H, J=6.9 Hz), 1.23–1.20 (m, 20H), 0.81 (t, 3H, J=6.9 Hz); $^{13}$C NMR (CD$_3$OD, 100 MHZ) δ 198.8, 130.9, 130.8, 41.6, 33.1, 30.9, 30.8(2), 30.6, 30.5, 30.4(2), 30.3, 30.2, 28.1(2), 26.5, 23.8, 14.5; IR (film) $v_{max}$ 3083, 2924, 2854, 2102, 1644, 1463, 1372, 1144 cm$^{-1}$; FABHRMS (NBA) m/z 307.2738 (C$_{19}$H$_{34}$N$_2$O+H$^+$ requires 307.2749).

Synthesis of N-Amino-9Z-octadecenamide (22)

A solution of oleic acid (250 μL, 0.79 mmol, 1 equivalent) and hydrazine monohydrate (42 μL, 0.87 mmol, 1.1 equivalents) in anhydrous CH$_2$Cl$_2$ (12 mL) under N$_2$ at 0° C. was treated with EDCI (267 mg, 0.90 mmol, 1.1 equivalents) and DMAP (20 mg, 0.16 mmol, 0.21 equivalent) before the reaction mixture was allowed to stir at 25° C. for 7 hours. Another portion of EDCI (269 mg, 0.91 mmol, 1.1 equivalents) was added and the reaction was stirred at 25° C. for an additional 12 hours before the solvent was removed in vacuo. Chromatography (SiO$_2$, 3×18 cm, 20–100% EtOAc-hexane gradient elution) afforded 22 (123 mg, 52%) as a white solid: mp 95°–96° C.; $^1$H NMR (CDCl$_3$, 400 MHZ) δ 8.94 (s, 1H), 5.36–5.27 (m, 2H), 2.23 (t, 2H, J=7.6 Hz), 1.98 (m, 4H), 1.63 (p, 2H, J=7.0 Hz), 1.27–1.24 (m, 20H), 0.86 (t, 3H, J=6.7 Hz); $^{13}$C NMR (CDCl$_3$, 100 MHZ) δ 169.7, 130.0, 129.7, 34.1, 31.9, 29.8, 29.7, 29.5, 29.3(2), 29.23, 29.19, 29.12, 27.21, 27.17, 25.4, 22.7, 14.1; IR (film) ν$_{max}$ 3201, 2917, 2848, 1595, 1410, 1184, 1090, 927, 717, 671 cm$^{-1}$; FABHRMS (NBA-NaI) m/z 297.2916 (C$_{18}$H$_{36}$N$_2$O+H$^+$ requires 297.2906).

Synthesis of Methyl 10Z-Nonadecenoate (23)

A solution of silver benzoate (21.8 mg, 0.095 mmol, 0.1 equivalent) and anhydrous Et$_3$N (0.19 mL, 1.36 mmol, 1.4 equivalents) was added dropwise to a solution of 1-diazo-10Z-nonadecen-2-one (21, 298 mg, 0.97 mmol, 1 equivalent) in anhydrous CH$_3$OH (1.5 mL) under N$_2$ and the reaction was stirred at 25° C. for 2.5 hours. The reaction mixture was diluted with EtOAc (30 mL) and washed with 1N aqueous HCl (30 mL) and saturated aqueous NaHCO$_3$ (30 mL). The organic layers were dried (Na$_2$SO$_4$), filtered, and concentrated in vacuo. Chromatography (SiO$_2$, 3×15 cm, 1–5% EtOAc-hexane gradient elution) afforded 23 (246 mg, 82%) as a clear oil: $^1$H NMR (CDCl$_3$, 400 MHZ) δ 5.35–5.27 (m, 2H), 3.63 (s, 3H), 2.27 (t, 2H, J=7.6 Hz), 1.97 (m, 4H), 1.59 (p, 2H, J=7.3 Hz), 1.26–1.24 (m, 22H), 0.85 (t, 3H, J=6.8 Hz); $^{13}$C NMR (CDCl$_3$, 100 MHZ) δ 174.3, 129.9, 129.8, 51.4, 34.1, 31.9, 29.74, 29.70, 29.5, 29.3(2), 29.2(2), 29.1(2), 27.2(2), 24.9, 22.6, 14.1; IR (film) ν$_{max}$ 2925, 2854, 1744, 1465, 1436, 719 cm$^{-1}$; FABHRMS (NBA-NaI) m/z 311.2969 (C$_{20}$H$_{38}$O$_2$+H$^+$ requires 311.2950).

Synthesis of 10Z-Nonadecenoic Acid (24)

A solution of 23 (620 mg, 2.0 mmol, 1 equivalent) in THF—CH$_3$OH—H$_2$O (3:1:1; 7 mL) at 25° C. was treated with LiOH.H$_2$O (250 mg, 5.96 mmol, 3 equivalents) and the reaction mixture was stirred for 3 hours. The reaction mixture was acidified with the addition of 1N aqueous HCl (60 mL) and the aqueous layer was extracted with EtOAc (2×60 mL). The organic layers were dried (Na$_2$SO$_4$), filtered, and concentrated in vacuo. Chromatography (SiO$_2$, 4×15 cm, 10–100% EtOAc-hexane gradient elution) afforded 24 (510 mg, 86%) as a pale yellow oil: $^1$H NMR (CDCl$_3$, 400 MHZ) δ 5.37–5.28 (m, 2H), 2.32 (t, 2H, J=7.5 Hz), 1.98 (m, 4H), 1.61 (p, 2H, J=7.3 Hz), 1.27–1.25 (m, 22H), 0.86 (t, 3H, J=6.9 Hz); $^{13}$C NMR (CDCl$_3$, 100 MHZ δ 180.4, 130.0, 129.8, 34.1, 31.9, 29.8, 29.7, 29.5, 29.3(2), 29.2(2), 29.0(2), 27.20, 27.17, 24.6, 22.7, 14.1; IR (film) ν$_{max}$ 2925, 2854, 1711, 1466, 1412, 1260, 1093, 1019, 938, 801, 722 cm$^{-1}$; FABHRMS (NBA-NaI) m/z 319.2605 (C$_{19}$H$_{36}$O$_2$+Na$^+$ requires 319.2613). This compound can alternatively be prepared by the method of Doleshall, G. *Tetrahedron Lett.* 1980, 21, 4183–4186.

Synthesis of 2-Hydroxy-10Z-nonadecenoic Acid (25)

A fresh solution of LDA was prepared at −55° C. under Ar from diisopropylamine (0.4 mL, 2.9 mmol, 4.5 equivalents), and n-BuLi (2.3M, 1.1 mL, 2.5 mmol, 4 equivalents) in anhydrous THF (2 mL). A solution of 10Z-nonadecenoic acid (24, 188 mg, 0.63 mmol, 1 equivalent) and anhydrous HMPA (0.11 mL, 0.63 mmol, 1 equivalent) in THF (0.5 mL) was added dropwise to the LDA solution at −55° C. The reaction mixture was allowed to warm gradually to 25° C. and was warmed at 50° C. for 30 minutes. After the reaction mixture was recooled to 25° C., O$_2$ was bubbled through the solution for 20 minutes. The mixture was treated with 1N aqueous HCl (30 mL) and the aqueous layer was extracted with EtOAc (3×30 mL). The organic layers were dried (Na$_2$SO$_4$), filtered, and concentrated in vacuo. Chromatography (SiO$_2$, 2×13 cm, 50–100% EtOAc-hexane gradient elution) afforded 25 (96 mg, 49%) as a white solid: mp 53°–54° C.; $^1$H NMR (CDCl$_3$, 400 MHZ) δ 5.36–5.28 (m, 2H), 4.24 (dd, 1H, J=7.5 Hz, 7.6 Hz), 1.98 (m, 4H), 1.83 (m, 1H), 1.67 (m, 1H), 1.47–1.24 (m, 22H), 0.86 (t, 3H, J=6.8 Hz); $^{13}$C NMR (CDCl$_3$, 100 MHZ δ 179.8, 130.0, 129.7, 70.2, 34.2, 31.9, 29.8, 29.7, 29.5, 29.33, 29.31(2), 29.22, 29.19, 27.20, 27.16, 24.8, 22.7, 14.1; IR (film) ν$_{max}$ 3512, 2917, 2849, 1704, 1467, 1293, 1274, 1251, 1212, 1143, 1079, 1041, 918, 726, 648 cm$^{-1}$; FABHRMS (NBA-NaI) m/z 335.2574 (C$_{19}$H$_{35}$O$_3$+Na$^+$ requires 335.2562).

Synthesis of 2-Hydroxy-10Z-nonadecenamide (26)

A solution of 25 (71 mg, 0.23 mmol, 1 equivalent) in anhydrous CH$_2$Cl$_2$ (1.5 mL) under N$_2$ was cooled to 0° C. and treated dropwise with oxalyl chloride (2M in CH$_2$Cl$_2$, 0.34 mL, 0.68 mmol, 3 equivalents). The reaction mixture was allowed to warm to 25° C. and was stirred for 3 hours in the dark. The solvent was removed in vacuo, the residue was cooled to 0° C., and excess concentrated aqueous NH$_4$OH (2 mL) was added. Chromatography (SiO$_2$, 1.5×13 cm, 50–66% EtOAc-hexane gradient elution) afforded 26 (53 mg, 75%) as a white solid: mp 101°–102° C.; $^1$H NMR (CDCl$_3$, 400 MHZ) δ 6.36 (br, 1H), 5.65 (br, 1H), 5.36–5.28 (m, 2H), 4.12 (dd, 1H, J=7.9 Hz, 8.0 Hz), 1.99 (m, 4H), 1.81 (m, 1H), 1.63 (m, 1H), 1.43–1.24 (m, 22H), 0.86 (t, 3H, J=6.9 Hz); $^{13}$C NMR (CDCl$_3$, 100 MHZ) δ 176.6, 130.0, 129.8, 71.9, 34.8, 31.9, 29.8, 29.7, 29.5, 29.4, 29.3(3), 29.2, 27.20, 27.16, 24.9, 22.7, 14.1; IR (film) ν$_{max}$ 3383, 3290, 2917, 2849, 1644, 1467, 1426, 1331, 1075 cm$^{-1}$; FABHRMS (NBA-NaI) m/z 334.2731 (C$_{19}$H$_{37}$NO$_2$+Na$^+$ requires 334.2722).

Synthesis of 8Z-Heptadecenoic acid (27)

A solution of 5 (66 mg, 0.26 mmol, 1 equivalent) and 2-methyl-2-butene (1.6 mL, 15.1 mmol, 58 equivalents) in tBuOH (6.5 mL) at 25° C. under N$_2$ was treated dropwise with a solution of NaClO$_2$ (80%, 208 mg, 2.3 mmol, 9 equivalents) and NaH$_2$PO$_4$.H$_2$O (250 mg, 1.8 mmol, 7 equivalents) in deionized H$_2$O (2.5 mL). The reaction mixture was allowed to stir for an additional 15 minutes before being concentrated in vacuo. The residue was treated with water (30 mL) and the aqueous layer was extracted with EtOAc (3× 30 mL). The organic layers were dried (Na$_2$SO$_4$), filtered, and concentrated in vacuo. Chromatography (SiO$_2$, 2×13 cm, 10–20% EtOAc-hexane gradient elution) afforded 27 (66 mg, 95%) as a clear oil. Spectral properties agree with those described in the S literature Miralles et al., *Lipids* 1995, 30, 459–466; Couderc et al., *Lipids* 1995, 30, 691–699.

3-Oxo-2-(triphenylphosphoranylidene)octadecanoate (28)

A solution of palmitic acid (103 mg, 0.40 mmol, 1 equivalent) in anhydrous CH$_2$Cl$_2$ (2 mL) under N$_2$ was cooled to 0° C. and treated with oxalyl chloride (2M in CH$_2$Cl$_2$, 0.6 mL, 1.2 mmol, 3 equivalents). The solution was allowed to stir at 25° C. for 3 hours before the solvent was removed in vacuo. A solution of tert-butyl (triphenylphosphoranylidene)acetate (Cooke et al., *J. Org. Chem.* 1982, 47, 4955–4963) 29, 167 mg, 0.44 mmol, 1.1 equivalents) and bis(trimethylsilyl)acetamide (195 μL, 0.79 mmol, 2 equivalents), in anhydrous benzene (3 mL) at 5° C. was treated dropwise with a solution of the crude acid chloride in benzene (3 mL). The reaction mixture was allowed to warm to 25° C. and was stirred 1.5 hours before the solvent was removed in vacuo. Chromatography (SiO$_2$, 2×15 cm, 10–20% EtOAc-hexane gradient elution) afforded 28 (193 mg, 78%) as a clear oil: $^1$H NMR (CDCl$_3$, 400 MHZ) δ 7.67–7.61 (m, 6H), 7.49–7.37 (m, 9H), 2.82 (t, 2H, J=7.6 Hz), 1.55 (p, 2H, J=7.0 Hz), 1.23–1.21 (m, 24H), 1.04 (s, 9H), 0.86 (t, 3H, J=6.8 Hz); $^{13}$C NMR (CDCl$_3$, 100 MHZ δ 197.9 (d, J=6 Hz), 167.3 (d, J=13 Hz), 132.9 (d, 6C, J=9 Hz), 131.3 (3), 128.4 (d, 6C, J=12 Hz), 127.4 (d, 3C, J=96 Hz), 78.4, 71.2 (d, J=114 Hz), 40.0, 31.9, 29.70(8), 29.66, 29.3, 28.1(3), 25.9, 22.7, 14.1; IR (film) $v_{max}$ 3426, 2923, 2852, 1665, 1551, 1438, 1363, 1302, 1173, 1106, 1081, 746, 690 cm$^{-1}$; FABHRMS (NBA-CsI) m/z 615.3959 ($C_{40}H_{55}O_3P+H^+$ requires 615.3967).

Determination of Binding Constants

The potency of the these compounds against oleamide hydrolysis was evaluated using an ion-selective ammonia electrode (ATI/Orion) to directly measure ammonia formation as the product of the reaction. All $K_i$s except for that of oleic acid were determined by the Dixon method. (X intercepts of weighted linear fits of [I] versus 1/Rate plots at a constant substrate concentration were converted to $K_i$'s using the formula $K_i=-X_{int}/[1+[S]/K_m]$.) The oleic acid $K_i$ was obtained from a non-linear weighted least-squares fit of rate versus substrate and inhibitor concentrations. The assays were done with constant stirring in 10 mL 50 mM CAPS buffer (Sigma) adjusted to pH 10.0, the pH at which the rate of enzymatically catalyzed oleamide hydrolysis is maximal. In all cases which involved Dixon analysis, the substrate concentration was 100 μM. The oleic acid $K_i$ was determined over a range of substrate concentrations from 10 to 100 μM. Substrate and inhibitors were dissolved in DMSO prior to addition to the 50 mM CAPS buffer, generating a final DMSO assay concentration of 1.67%. Concentrations of up to 20% DMSO exhibited only minor effects upon the rate. The enzyme concentration was adjusted to produce a rate of roughly 0.2 μM/min in the absence of inhibitor and the rate of ammonia production observed over a period of 7 to 10 minutes.

The enzyme was used as a crude, heterogenous, membrane-containing preparation from rat liver. Enzyme boiled for 5 minutes demonstrated no activity. Within solubility limits, all inhibitors achieved 100% inhibition of activity at concentrations of greater than 100 $K_i$. No detectable activity was found in the absence of added oleamide. Likewise, only a very minimal rate of ammonia production from 100 μM oleamide was detected in the absence of enzyme at this pH. This suggests that the catalytic oleamide hydrolysis activity observed in this crude enzyme preparation arises from a single protein.

The $K_m$ for oleamide was determined as the average $K_m$ obtained from four independent assays. Each independent $K_m$ was obtained from weighted linear fit of data in a Lineweaver-Burke plot. A fifth concurring $K_m$ was obtained as a result of the determination of oleic acid inhibition by non-linear methods. The rate data was fit with the standard Michaelis-Menten kinetic equation. (The equation for the rate of Ping Pong Bi Bi kinetics collapses to the simple Michaelis-Menten-like equation when the concentration of the second substrate, in this case water, is constant). In the range 30–100 μM, the reaction rate has essentially a zero order dependence on substrate concentration.

Because we have not yet been able to determine the amount of oleamide hydrolase present in the enzyme sample, we do not present values for $V_{max}$ here. Our inhibition data suggests that the enzyme concentration is lower than 2 nM, since higher enzyme concentrations would have caused significant depletion of inhibitor in solution, causing the apparent $K_i$ to be measured as [E]/2 in the limiting case of [E]>>$K_i$. Since 1 nM was the lowest inhibition constant measured, [E]<2 nM.

Error values presented with $K_i$s should be considered goodness-of-fit estimates derived from propagation of errors treatment of data. They are not necessarily an indication of reproducibility. However, in cases where experiments were repeated, results were within statistical agreement as predicted by the apparent error values given here.

pH-Rate Dependence

Crude enzyme was added to a solution of 200 μM oleamide (approximately the solubility limit) 1 in 20 mL buffer at the appropriate pH, containing 5% DMSO. (Concentrations of up to 20% DMSO had only minimal effect on enzyme rates.) A 50 mM sodium citrate/Bis-tris buffer was used for data points in the pH 4–9 range. A 50 mM Bis-tris/CAPS was used for data points in the 8–11 range. At pH 12, the solution was assumed to be self-buffering. At periodic time intervals, 1 mL aliquots were removed and diluted with 9 mL pH 14 buffer. Ammonia concentrations were measured with an ion-selective ammonia electrode (Orion) connected to a 720A meter (Orion), calibrated against known standards. The rate was obtained from the linear portion of the curve which was fit using a standard least-squares procedure. These rates were replotted against pH and fit with the equation in FIG. 12 (Fersht, A., *Enzyme Structure and Mechanism*; W. H. Freeman and Co.: New York, 1985, pp 157 Connors, K. A., *Binding Constants*; Wiley: New York, 1987, pp 385–395) by a weighted non-linear least-squares method (Connors, K. A., *Binding Constants*; Wiley: New York, 1987, pp 385–395).

In cases where two pKa's are close together (less than one unit) there will be substantial mixing of various species of enzyme present in solution. Under such conditions, manifestation of the theoretical rate maximum for that species may never actually be observed because the most active species of enzyme may never reach a high degree of abundance. It is for this reason that simple graphical methods of determination of pKa's may disagree with the values of 9.7 and 10.3 pH units presented here.

Liver Plasma Membrane Prep, Large Scale (12–14 Rat Livers)

Twelve to fourteen rat livers were sectioned and placed in 300 mL of 1 mM NaHCO$_3$. The solution of diced liver was strained and washed with additional 300 mL of 1 mM NaHCO$_3$. Any conspicuous connective tissue was removed. The liver was transferred to a fresh 800 mL of 1 mM NaHCO$_3$, stirred and then transferred in 400 mL aliquots to a blender. Blended liver aliquots were combined and filtered through 8 layers of cheesecloth. This was diluted to 1.0 L with 1 mM NaHCO$_3$ and centrifuged at 6000 rpm for 20 minutes at 4° C. (Beckman JA-17 rotor). The supernatant was decanted, the pellets resuspended in 1 mM NaHCO$_3$, combined and dounce homogenized. Centrifugation, decantation and resuspension/homogenization were repeated to give a final volume of approximately 90 mL. The homogenate was added to 2 volume equivalents of 67% sucrose, mixed thoroughly, and transferred to ultracentrifuge compatible tubes. The tubes were topped with 30% sucrose and spun at 27,000 for 2 hours (SW-28 rotor). The middle yellow band was removed from the sucrose gradient, combined, resuspended in 1 mM NaHCO$_3$, and dounce homogenized. The sample was further centrifuged at 17,000 rpm for 45 minutes at 4° C. (JA-17 rotor). The supernatant was removed, the pellets resuspended in 100 mM Na$_2$CO$_3$, dounce homogenized and left on ice for 30 minutes. The solution was centrifuged at 27,000 rpm for 1 hour (SW-28 rotor), the supernatant was decanted and the pellet resuspended in 15 mL of 50 mM Tris HCl, pH 7.4 with 1 mM EDTA, and homogenized with a dounce homogenizer. This material was divided into multiple aliquots and frozen at −78° C. until use. Each enzyme sample was frozen once only.

What is claimed is:

1. An inhibitor of oleamide hydrolase, said inhibitor comprising a head group and a hydrocarbon tail covalently linked to said head group, wherein said head group includes an electrophilic carbonyl and is selected from a group consisting of radicals represented by the following structures:

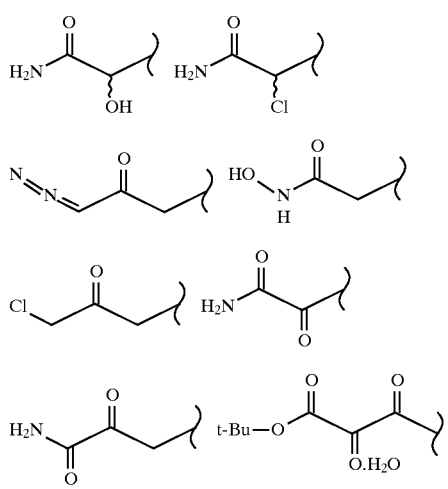

and wherein said hydrocarbon tail is selected from a group consisting of radicals represented by the following structures:

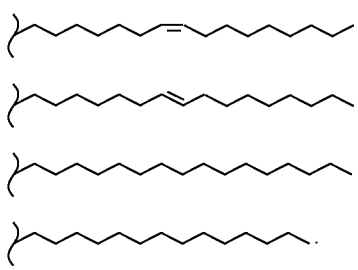

2. An inhibitor of oleamide hydrolase as described in claim 1 represented by the following structure:

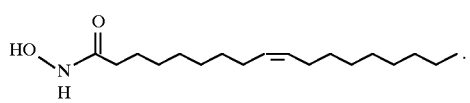

3. An inhibitor of oleamide hydrolase as described in claim 1 represented by the following structure:

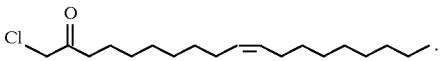

4. An inhibitor of oleamide hydrolase as described in claim 1 represented by the following structure:

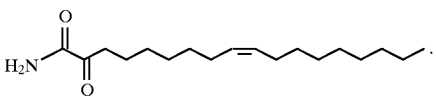

5. An inhibitor of oleamide hydrolase as described in claim 1 represented by the following structure:

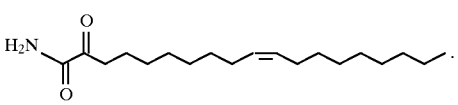

6. An inhibitor of oleamide hydrolase as described in claim 1 represented by the following structure:

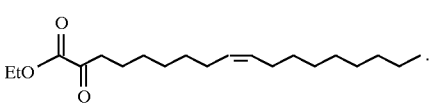

7. An inhibitor of oleamide hydrolase as described in claim 1 represented by the following structure:

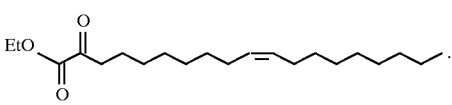

8. An inhibitor of oleamide hydrolase as described in claim 1 represented by the following structure:

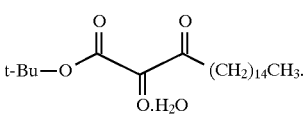

9. An inhibitor of oleamide hydrolase as described in claim 1 represented by the following structure:

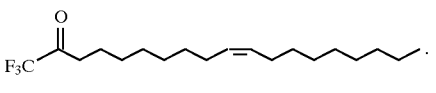

10. An inhibitor of oleamide hydrolase as described in claim 1 represented by the following structure:

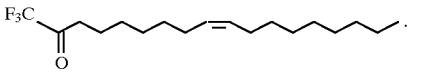

11. An inhibitor of oleamide hydrolase as described in claim 1 represented by the following structure:

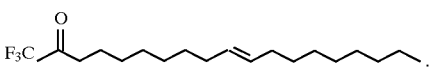

12. An inhibitor of oleamide hydrolase as described in claim 1 represented by the following structure:

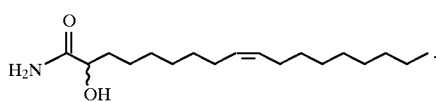

13. An inhibitor of oleamide hydrolase as described in claim 1 represented by the following structure:

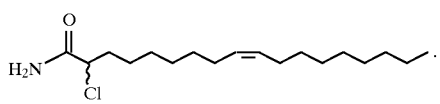

14. An inhibitor of oleamide hydrolase as described in claim 1 wherein said head group is a fatty acid ester and includes two or more electrophilic carbonyls and is selected from a group consisting of radicals represented by the following structures:

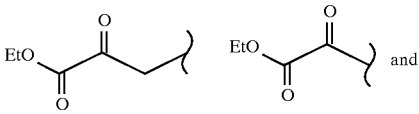

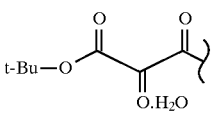

and wherein said hydrocarbon tail includes at least one unsaturation.

* * * * *